(12) United States Patent
Polytaridis et al.

(10) Patent No.: US 9,375,065 B2
(45) Date of Patent: Jun. 28, 2016

(54) APPARATUS AND METHODS FOR MAINTAINING A MEDICAL DEVICE IN A CLEAN AND DISINFECTED STATE, AND FOR CLEANING AND DISINFECTING A MEDICAL DEVICE

(71) Applicant: DexCom, Inc., San Diego, CA (US)

(72) Inventors: Nicholas Polytaridis, San Diego, CA (US); David J. Carner, Fallbrook, CA (US); Jacob S. Leach, San Diego, CA (US); Christina Orsini, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 14/505,451

(22) Filed: Oct. 2, 2014

(65) Prior Publication Data
US 2015/0108185 A1   Apr. 23, 2015

Related U.S. Application Data

(60) Provisional application No. 61/893,822, filed on Oct. 21, 2013.

(51) Int. Cl.
| | |
|---|---|
| *A61L 2/00* | (2006.01) |
| *A61B 1/32* | (2006.01) |
| *A61B 19/02* | (2006.01) |
| *A45C 11/00* | (2006.01) |
| *A61B 5/145* | (2006.01) |

(52) U.S. Cl.
CPC .............. *A45C 11/00* (2013.01); *A61B 5/14532* (2013.01); *A45C 2011/003* (2013.01); *A45C 2011/007* (2013.01); *A61B 2562/245* (2013.01); *A61B 2562/247* (2013.01); *Y10T 29/49826* (2015.01)

(58) Field of Classification Search
CPC ...... A61B 17/3423; A61B 19/38; B01L 9/06; B62D 21/0233
USPC .......... 600/207–208; 433/167; 206/778, 63.5, 206/219, 518; 53/467, 492; 422/1, 28
See application file for complete search history.

(56) References Cited

U.S. PATENT DOCUMENTS

| | | | |
|---|---|---|---|
| 2009/0262492 A1 | 10/2009 | Whitchurch et al. | |
| 2011/0073608 A1 | 3/2011 | Richardson et al. | |
| 2012/0110824 A1* | 5/2012 | Smith .............. | A61B 17/00234 29/464 |
| 2012/0261306 A1 | 10/2012 | Richardson et al. | |
| 2014/0188398 A1 | 7/2014 | Cohen et al. | |

OTHER PUBLICATIONS

Aoconox, 2006. Tergazyme Technical Bulletin, Fax Document #0413. Tergazyme (TM) Enzyme-Active Powdered Detergent.

* cited by examiner

*Primary Examiner* — Monzer R Chorbaji
(74) *Attorney, Agent, or Firm* — Knobbe Martens Olson & Bear, LLP

(57) ABSTRACT

Sleeves and cases for protecting medical devices against contamination, and methods for cleaning and disinfecting medical devices are provided. The various embodiments enable a single medical device to be used by more than one patient successively while reducing the risk of disease transmission from patient to patient.

25 Claims, 16 Drawing Sheets

APPARATUS AND METHODS FOR MAINTAINING A MEDICAL DEVICE IN A CLEAN AND DISINFECTED STATE, AND FOR CLEANING AND DISINFECTING A MEDICAL DEVICE

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of priority of U.S. Provisional Application No. 61/893,822 filed Oct. 21, 2013. The aforementioned application is incorporated by reference herein in its entirety, and is hereby expressly made a part of this specification.

TECHNICAL FIELD

The present invention relates to medical devices, and, more particularly to maintaining cleanliness in such devices and to cleaning such devices.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter that transmits measurement data to a receiver that processes and displays information based on the measurements. Such sensor systems are sometimes referred to as continuous glucose monitors (CGMs).

In certain scenarios, certain components of a CGM may be used by more than one person. For example, diabetes patients may wish to try a CGM for a limited time on a trial basis, such as when a patient tests a CGM for the first time before committing to using one on a more permanent basis, or when a patient who currently uses a CGM wishes to try a new model, brand, etc. In these scenarios, it is desirable for the CGM to be cleaned and disinfected before it is passed to each patient in order to address concerns associated with blood-borne pathogen disease transmission.

SUMMARY

The present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

In a first aspect, which is generally applicable (i.e. independently combinable with any of the aspects or embodiments identified herein), particularly with any other embodiment of the first aspect, certain of the present embodiments comprise an enclosure for an electronic medical device. The enclosure comprises a sleeve configured to receive an electronic medical device having a port. The enclosure further comprises a first opening in the sleeve sized and configured to allow for insertion of the electronic medical device into the sleeve and removal of the electronic medical device from the sleeve. The enclosure further comprises a second opening in the sleeve, the second opening being located so as to permit access to the port when the electronic medical device is received within the sleeve. The enclosure further comprises a first cover configured to adhere to a first portion of the sleeve and to cover the first opening. The enclosure further comprises a second cover configured to adhere to a second portion of the sleeve and to cover the second opening.

In an embodiment of the first aspect, the enclosure further comprises a first adhesive located and configured to secure the first cover to the sleeve at the first portion.

In an embodiment of the first aspect, the enclosure further comprises a second adhesive located and configured to secure the second cover to the sleeve at the second portion.

In an embodiment of the first aspect, the first adhesive comprises a first peel strength, the second adhesive comprises a second peel strength, and the first peel strength is different than the second peel strength.

In an embodiment of the first aspect, the first peel strength is greater than the second peel strength.

In an embodiment of the first aspect, the first peel strength is great enough to prevent separation of the first cover from the sleeve without tearing the sleeve.

In an embodiment of the first aspect, the port is at least one of a charging port or a communication port.

In an embodiment of the first aspect, the communication port is a USB port.

In an embodiment of the first aspect, the sleeve comprises a material selected from the group consisting of: polyurethane, polyethylene, and low density polyethylene.

In an embodiment of the first aspect, the sleeve comprises a first portion comprising a first material and a second portion comprising a second material.

In an embodiment of the first aspect, the second material has greater stiffness than the first material.

In an embodiment of the first aspect, the first portion comprises a material selected from the group consisting of: polyurethane, polyethylene, and low density polyethylene.

In an embodiment of the first aspect, the second portion comprises a material selected from the group consisting of: polycarbonate and acrylonitrile butadiene styrene (ABS).

In an embodiment of the first aspect, the second portion is configured to provide access to the port.

In an embodiment of the first aspect, the first opening is surrounded by the first portion, and wherein the second opening is surrounded by the second portion.

In an embodiment of the first aspect, the first opening comprises a first slit that extends in a longitudinal direction, and a second slit that extends in a transverse direction.

In an embodiment of the first aspect, a first end of the first slit corresponds to a lengthwise center of the second slit.

In an embodiment of the first aspect, the electronic medical device is configured to display continuous glucose concentration data over a time period.

In a second aspect, which is generally applicable (i.e. independently combinable with any of the aspects or embodiments identified herein), particularly with any other embodiment of the second aspect, certain of the present embodiments comprise a method for reprocessing a reusable electronic medical device. The method comprises receiving an electronic medical device from a first user, wherein the electronic medical device is contained in a first protective enclosure. The method further comprises removing the electronic medical device from the first protective enclosure. The method further comprises inserting the electronic medical device into a second protective enclosure through an opening in the second protective enclosure. The method further comprises adhering a cover to the second protective enclosure over the opening such that the cover cannot be separated from the second protective enclosure without damaging the second protective enclosure. The method further comprises providing the electronic medical device contained within the second protective enclosure to a second user.

In an embodiment of the second aspect, the method further comprises creating a disinfected field, wherein removing the electronic medical device from the first protective enclosure and placing the electronic medical device in a second protective enclosure are performed in the disinfected field.

In an embodiment of the second aspect, removing the electronic medical device from the first protective enclosure requires tearing the first protective enclosure.

In an embodiment of the second aspect, the method further comprises cleaning and disinfecting the electronic medical device.

In an embodiment of the second aspect, the electronic medical device is configured to display continuous glucose concentration data over a time period.

In a third aspect, which is generally applicable (i.e. independently combinable with any of the aspects or embodiments identified herein), particularly with any other embodiment of the third aspect, certain of the present embodiments comprise a case for protecting an electronic medical device. The case comprises a housing defining a cavity configured to receive an electronic medical device having a port. The housing comprises an opening located and configured to allow access to the port when the electronic medical device is contained within the housing. The housing further comprises a lock, which, when in a locked position, is configured to prevent opening of the housing to thereby selectively deter removal of the electronic medical device from the housing.

In an embodiment of the third aspect, unlocking the lock enables removal of the electronic medical device from the housing.

An embodiment of the third aspect comprises the case in combination with a key configured to lock and unlock the lock.

In an embodiment of the third aspect, the housing comprises a first portion and a second portion, and when the first and second portions engage one another and the lock is in the locked position, the first and second portions cannot be separated from one another without damaging at least one of the first and second portions.

In an embodiment of the third aspect, the housing, when in a closed and locked configuration, meets the IPX7 standard with respect to water penetration.

In an embodiment of the third aspect, the housing comprises a material selected from the group consisting of: polycarbonate and acrylonitrile butadiene styrene (ABS).

In an embodiment of the third aspect, the electronic medical device comprises electronics and a display.

In an embodiment of the third aspect, the electronic medical device is configured to display continuous glucose concentration data over a time period.

In a fourth aspect, which is generally applicable (i.e. independently combinable with any of the aspects or embodiments identified herein), particularly with any other embodiment of the fourth aspect, certain of the present embodiments comprise a case for protecting an electronic medical device. The case comprises a housing defining a cavity configured to receive an electronic medical device having a port. The housing comprises a first portion, a second portion, and an opening located and configured to allow access to the port when the electronic medical device is contained within the housing. The housing further comprises at least one fastener configured to secure the first and second portions to one another and prevent access to the cavity to thereby selectively deter removal of the electronic medical device from the housing. The fastener, when in a secured position, cannot be removed from the first and second portions by hand.

In a fifth aspect, which is generally applicable (i.e. independently combinable with any of the aspects or embodiments identified herein), particularly with any other embodiment of the fifth aspect, certain of the present embodiments comprise a method for reprocessing a reusable electronic medical device. The method comprises receiving an electronic medical device from a first user, the electronic medical device including a water resistant protective coating. The method further comprises cleaning the electronic medical device to achieve a concentration in protein on surfaces of the electronic medical device of less than about 6.4 $\mu g/cm^2$, and a concentration in hemoglobin on surfaces of the electronic medical device of less than about 2.2 $\mu g/cm^2$. The method further comprises disinfecting the electronic medical device to achieve reductions in duck hepatitis B virus of at least about a 3 $\log_{10}$ reduction, in *klebsiella pneumonia* of least about a 6 $\log_{10}$ reduction, in *staphylococcus aureus* of least about a 6 $\log_{10}$ reduction, in *escherichia coli* of least about a 6 $\log_{10}$ reduction, in *pseudomonas aeruginosa* of least about a 6 $\log_{10}$ reduction, and in *mycobacterium terrae* of least about a 3 $\log_{10}$ reduction. At least one of cleaning the electronic medical device or disinfecting the electronic medical device comprises submerging the electronic medical device in a cleaning solution and/or a disinfecting solution. The method further comprises providing the cleaned and disinfected electronic medical device to a second user.

In an embodiment of the fifth aspect, the water resistant protective coating protects the electronic medical device from damage from liquid ingress.

In an embodiment of the fifth aspect, the method further comprises drying the electronic medical device.

In an embodiment of the fifth aspect, the electronic medical device includes at least electronics, a port, a display, and a speaker.

In an embodiment of the fifth aspect, the electronic medical device is configured to display continuous glucose concentration data over a time period.

In a seventh aspect, which is generally applicable (i.e. independently combinable with any of the aspects or embodiments identified herein), particularly with any other embodiment of the seventh aspect, certain of the present embodiments comprise a method for cleaning and disinfecting an electronic medical device. The method comprises cleaning the electronic medical device to achieve a concentration in protein on surfaces of the electronic medical device of less than about 6.4 µg/cm$^2$, and a concentration in hemoglobin on surfaces of the electronic medical device of less than about 2.2 µg/cm$^2$. The method further comprises disinfecting the electronic medical device to achieve reductions in duck hepatitis B virus of at least about 3 a $\log_{10}$ reduction, in *klebsiella pneumonia* of at least about a 6 $\log_{10}$ reduction, in *staphylococcus aureus* of at least about a 6 $\log_{10}$ reduction, in *escherichia coli* of at least about a 6 $\log_{10}$ reduction, in *pseudomonas aeruginosa* of at least about a 6 $\log_{10}$ reduction, and in *mycobacterium terrae* of at least about a 3 $\log_{10}$ reduction. The method further comprises drying the electronic medical device.

In an embodiment of the seventh aspect, the electronic medical device comprises at least electronics, a port, a display, and a speaker.

In an embodiment of the seventh aspect, the electronic medical device is configured to display continuous glucose concentration data over a time period.

In an eighth aspect, which is generally applicable (i.e. independently combinable with any of the aspects or embodiments identified herein), particularly with any other embodiment of the eighth aspect, certain of the present embodiments comprise a kit for covering and protecting an electronic medical device. The kit comprises a sleeve configured to receive an electronic medical device having a port. The sleeve comprises a first opening sized and configured to allow for insertion of the electronic medical device into the sleeve and removal of the electronic medical device from the sleeve. The sleeve further comprises a second opening in the sleeve, the second opening being located so as to permit access to the port when the electronic medical device is received within the sleeve. The kit further comprises a first closure configured to adhere to a first portion of the sleeve and to overlie and seal the first opening. The kit further comprises a second closure configured to adhere to a second portion of the sleeve and to overlie and seal the second opening.

In an embodiment of the eighth aspect, the kit further comprises an acoustic spacer configured to be interposed between the sleeve and the electronic medical device to create a space between the sleeve and the electronic medical device.

In an embodiment of the eighth aspect, each of the first and second closures includes an adhesive backing.

In an embodiment of the eighth aspect, the electronic medical device is configured to display continuous glucose concentration data over a time period.

BRIEF DESCRIPTION OF THE DRAWINGS

The present embodiments now will be discussed in detail with an emphasis on highlighting the advantageous features. These embodiments depict the novel and non-obvious apparatus and methods for maintaining a medical device in a clean and disinfected state, and for cleaning and disinfecting a medical device, shown in the accompanying drawings, which are for illustrative purposes only. These drawings include the following figures, in which like numerals indicate like parts.

DETAILED DESCRIPTION

Figure 1:
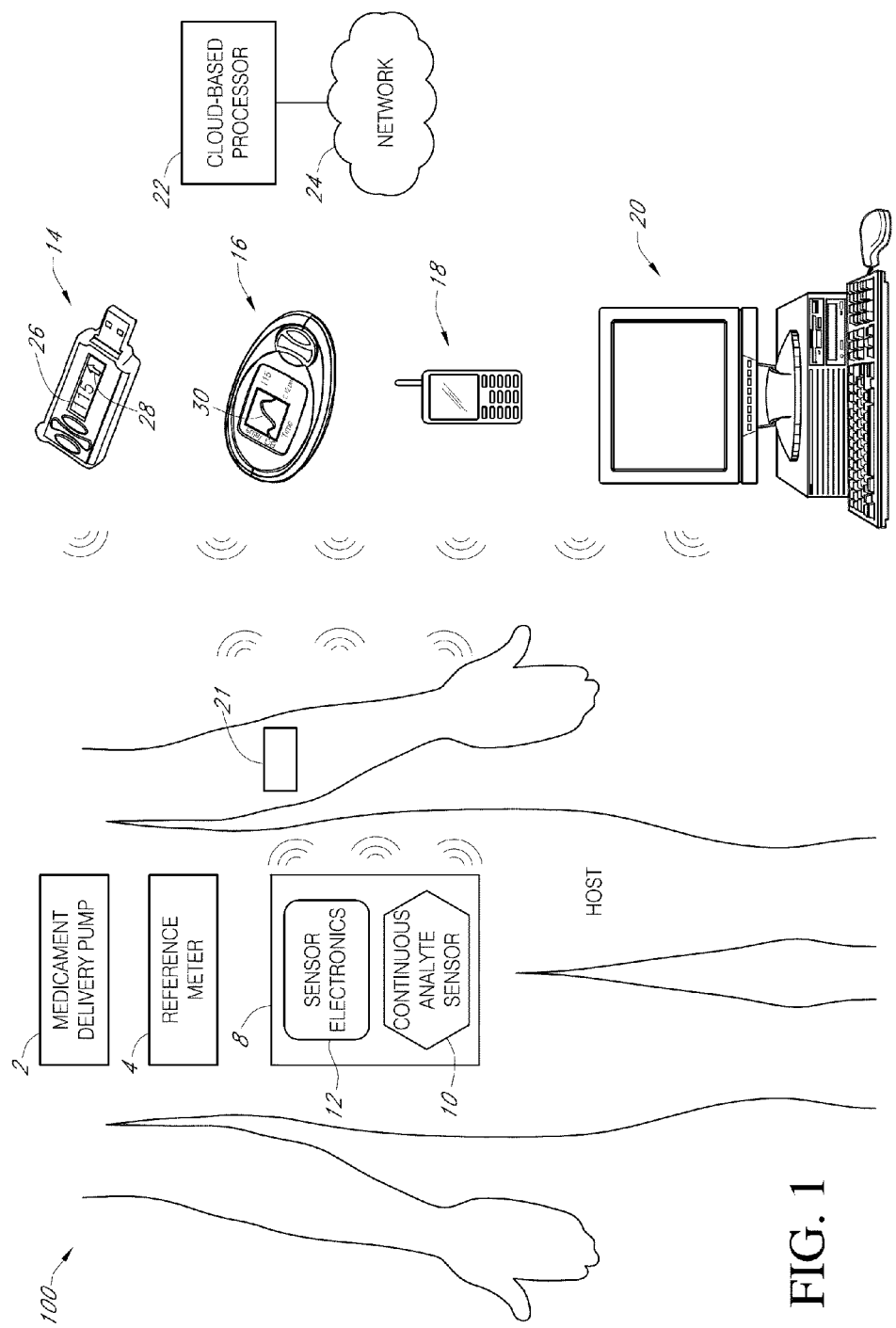
FIG. 1 is a schematic view of a continuous analyte sensor system attached to a host and communicating with other devices.

The following detailed description describes the present embodiments with reference to the drawings. In the drawings, reference numbers label elements of the present embodiments. These reference numbers are reproduced below in connection with the discussion of the corresponding drawing features.

The present embodiments are described below with reference to the figures. These figures, and their written descriptions, may indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

Sensor

The preferred embodiments relate to the use of an analyte sensor that measures a concentration of glucose or a substance indicative of the concentration or presence of the analyte. In some embodiments, the analyte sensor is a continuous device, for example a subcutaneous, transdermal, transcutaneous, and/or intravascular (e.g., intravenous) device. In some embodiments, the device can analyze a plurality of intermittent blood samples. The analyte sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The analyte sensor can use any known method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods of the preferred embodiments can be applied to any measurable analyte. In some preferred embodiments, the analyte sensor is a glucose sensor capable of measuring the concentration of glucose in a host. One example embodiment is described below, which utilizes an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Patent Publication No. US-2011-0027127-A1. In another preferred embodiment, the analyte sensor is a transcutaneous glucose sensor, such as described with reference to U.S. Patent Publication No. US-2006-0020187-A1. In yet another preferred embodiment, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1.

Deposition Techniques

The membrane system can be deposited on the exposed electroactive surfaces using any variety of known thin film techniques (for example, vapor deposition, spraying, printing (e.g., pad printing), electro-depositing, dipping, sputtering deposition, spin coating, powder coating, and the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art.

Analyte List

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to lactate or lactic acid; cardiac markers; ketone bodies; acetone; acetoacetic acid; beta hydroxybutyric acid; glucagon, acetyl Co A; intermediaries in the Citric Acid Cycle; choline, testosterone; creatinine; triglycerides; sodium; potassium; chloride; bicarbonate; total protein; alkaline phosphatase; calcium; phosphorus; $PO_2$; $PCO_2$; bilirubin (direct and total); red blood cell count; white blood cell count; hemoglobin; hematocrit; lymphocytes; monocytes; eosinophils; basophils; c-reactive protein; cryoglobulins; fibrinogens; ACTH; aldosterone; ammonia; beta-HCG; magnesium; copper; iron; total cholesterol; low density lipoproteins; high density lipoproteins; lipoprotein A; T4 (total and free); TSH; FSH; LH; ACTH; hepatitis BE antigen; hepatitis B surface antigen; hepatitis A antibody; hepatitis C antibody; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies A, S, C, and E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free B-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, *Entamoeba histolytica, enterovirus, Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae, Myoglobin, Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbonbased synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

High-Level CGM System Description

For illustrative purposes, reference will now be made to FIG. 1, which is an example environment in which some embodiments described herein may be implemented. Here, an analyte monitoring system 100 includes a continuous analyte sensor system 8. Continuous analyte sensor system 8 includes a sensor electronics module 12 and a continuous analyte sensor 10. The system 100 can also include other devices and/or sensors, such as a medicament delivery pump 2 and a reference analyte meter 4, as illustrated in FIG. 1. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate to sensor electronics module 12, but electronically coupled via inductive coupling or the like. Further, the sensor electronics module 12, medicament delivery pump 2, and/or analyte reference meter 4 may communicate with one or more additional devices, such as any or all of display devices 14, 16, 18, 20, and 21.

The system 100 of FIG. 1 also includes a cloud-based processor 22 configured to analyze analyte data, medicament delivery data, and/or other patient related data provided over network 24 directly or indirectly from one or more of sensor system 8, medicament delivery pump 2, reference analyte meter 4, and display devices 14-21. Based on the received data, the processor 22 can further process the data, generate reports providing statistic based on the processed data, trigger notifications to electronic devices associated with the host or caretaker of the host, or provide processed information to any of the other devices of FIG. 1. In some example implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

It should be understood that although the example implementation described with respect to FIG. 1 refers to analyte data being received by processor 22, other types of data processed and raw data may be received as well.

In some example implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, 20, and 21. The display devices 14, 16, 18, 20, and/or 21 may be configured for processing and presenting information, such sensor information transmitted by the sensor electronics module 12 for display at the display device. The display devices 14, 16, 18, 20, and 21 can also trigger alarms based on the analyte sensor data.

In FIG. 1, display device 14 is a key fob-like display device, display device 16 is a hand-held application-specific computing device 16 (e.g. the DexCom G4® Platinum receiver commercially available from DexCom, Inc.), display device 18 is a general purpose smart phone or tablet computing device 20 (e.g. an Apple® iPhone®, iPad®, or iPod Touch® commercially available from Apple, Inc.), display device 20 is a computer workstation 20, and display device 21 is any wearable. In some example implementations, the relatively small, key fob-like display device 14 may be a computing device embodied in a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the display device 18) and may be configured to display a limited set of displayable sensor information, such as a numerical value 26 and/or an arrow 28. In contrast, display devices 16, 18, and 20 can be larger display devices that can be capable of displaying a larger set of displayable information, such as a trend graph 30 depicted on the hand-held receiver 16 in addition to other information such as a numerical value and arrow.

It is understood that any other user equipment (e.g. computing devices) configured to at least present information (e.g., a medicament delivery information, discrete self-monitoring analyte readings, heart rate monitor, caloric intake monitor, and the like) can be used in addition or instead of those discussed with reference to FIG. 1.

In some example implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations of FIG. 1, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a DexCom G4® Platinum glucose sensor and transmitter commercially available from DexCom, Inc., for continuously monitoring a host's glucose levels.

As discussed above, medical devices may in some cases be used by more than one patient. For example, the medical device receiver 16 of FIG. 1 may be used by multiple patients on a trial basis so that each patient can determine whether a particular model of receiver is the right one for him or her before committing to buying one. To reduce the spread of disease, it is desirable for such medical devices to be in a clean and disinfected state when passed on to each patient. The present embodiments, described in detail below, provide various apparatus and methods for maintaining a medical device in a cleaned and disinfected state, and for cleaning and disinfecting a medical device after use.

Protective Sleeve

FIGS. 2-4A illustrate one embodiment of a protective sleeve 200 for receiving an electronic medical device 201 (FIG. 3A) to reduce the risk of contamination of the medical device 201. Under typical use, the sleeve 200 preferably resists penetration of contaminants into an interior of the sleeve 200 so that such contaminants cannot reach the medical device 201 contained within the sleeve 200. In some embodiments, the sleeve 200 may be designed for a single use, after which the sleeve 200 may be disposed of. In other embodiments, the sleeve 200 may be designed for multiple uses, which may comprise cleaning and disinfecting between uses.

Figure 2:
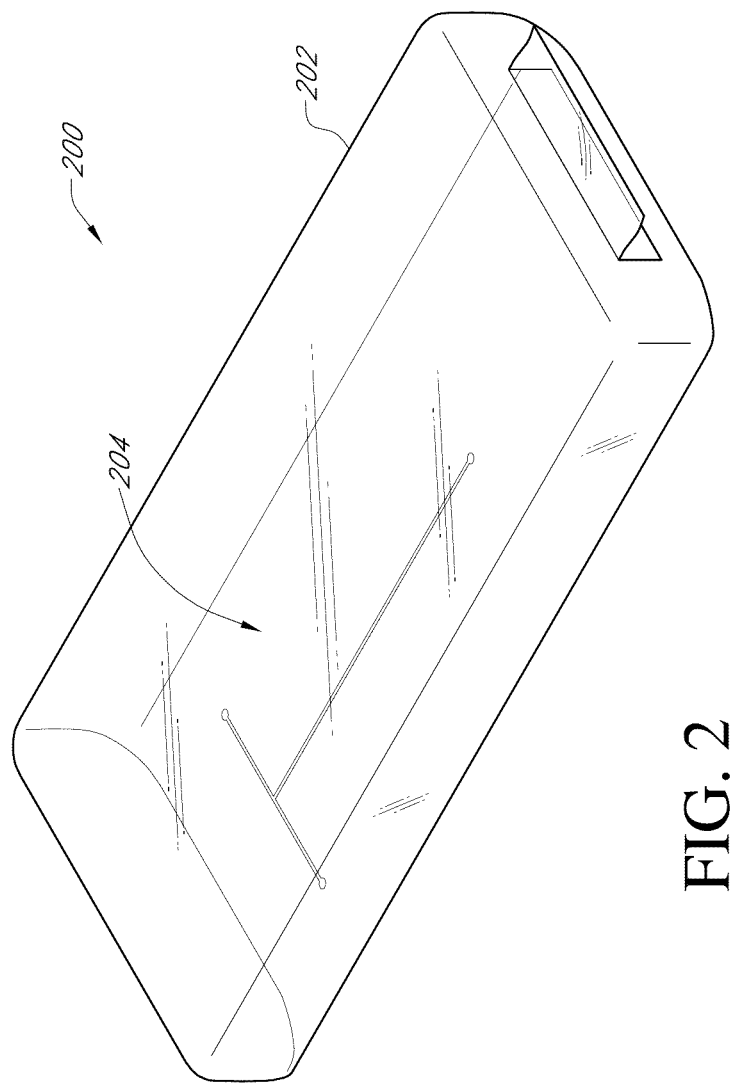
FIG. 2 is a rear perspective view of one embodiment of a protective sleeve for receiving a medical device.
Figure 3A:
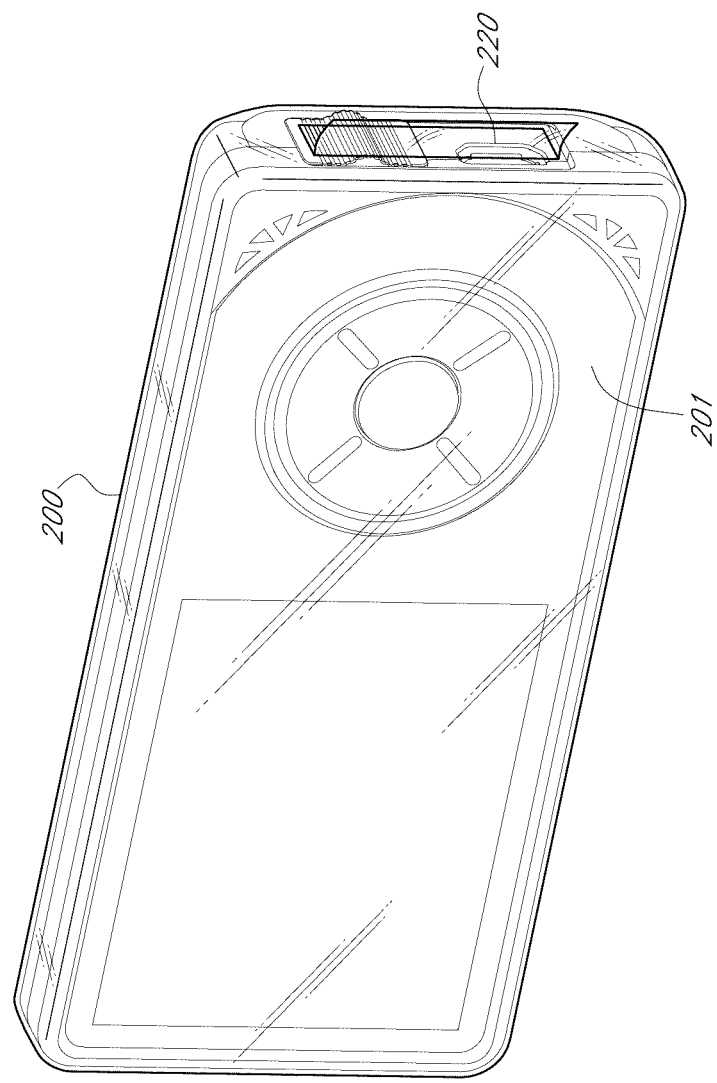
FIG. 3A is a front perspective view of the protective sleeve of FIG. 2 with a medical device received therein.
Figure 3B:
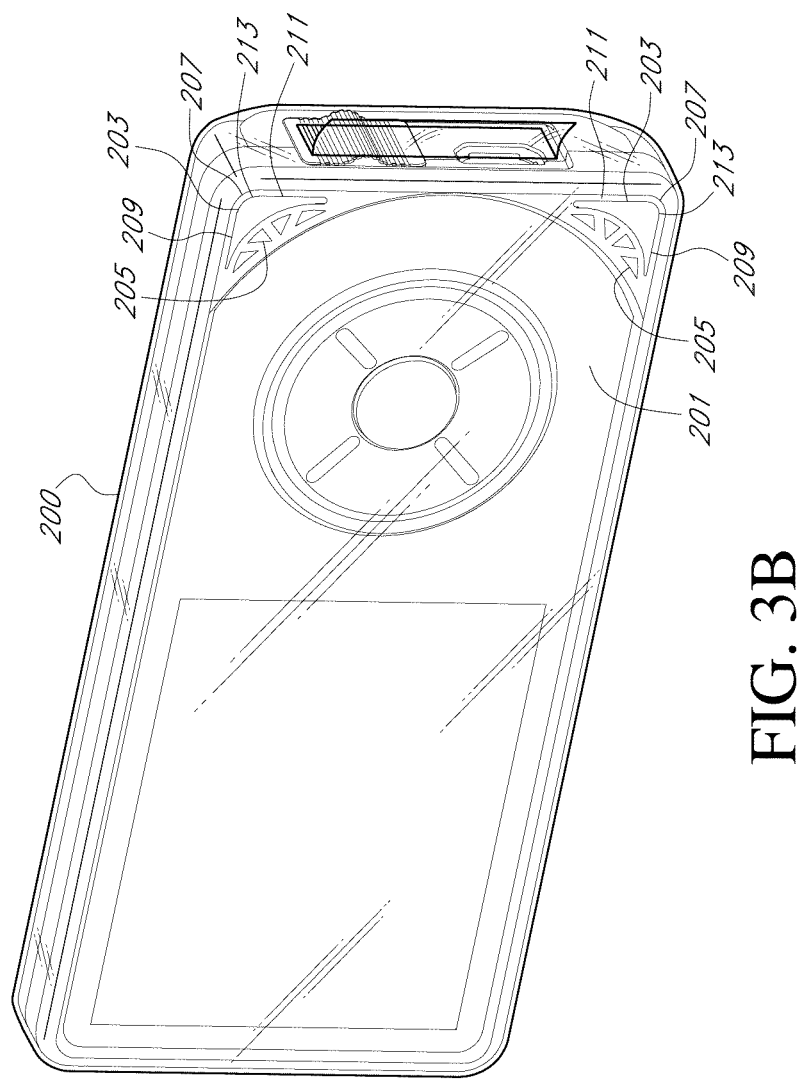
FIG. 3B is a front perspective view of the protective sleeve and the medical device of FIG. 3A in combination with acoustic spacers.

With reference to FIG. 2, the sleeve 200 comprises a body portion 202 defining an internal space 204 for receiving the medical device 201. The body portion 202 is sized and shaped such that it can be formed to have a shape such that the space 204 is substantially the same size and shape as the medical device 201, so that the sleeve 200 fits over the medical device 201 in a closely conforming fashion, as shown in FIGS. 3A and 3B. The body portion 202 may also be sized so that the space 204 is slightly smaller than the medical device 201, so that the sleeve 200 stretches in order to fit over the medical device 201 in a closely conforming fashion. In the illustrated embodiment, the sleeve 200 is shaped substantially as a rectangular parallelepiped when expanded, but in other embodiments the sleeve can be designed to have any shape to fit any of a variety of medical devices.

With reference to FIG. 4, a back panel 206 of the sleeve 200 includes an ingress/egress opening 208 through which the medical device 201 may be passed to insert the medical device 201 into the sleeve 200 and to withdraw the medical device 201 from the sleeve 200. In the illustrated embodiment, the opening 208 comprises a first slit 210 in the back panel 206 that runs substantially parallel to a longitudinal axis of the sleeve 200, and a second slit 212 in the back panel 206 that runs substantially perpendicular to the longitudinal axis of the sleeve 200, and which intersects a first end 214 of the first slit 210. The opening 208 is thus substantially T-shaped. However, in other embodiments the opening 208 can have any of a variety of configurations.

With further reference to FIG. 4, an end panel 216 of the sleeve 200 includes an access opening 218 through which one or more ports of the medical device 201 may be accessed. For example, the medical device 201 may include a Universal Serial Bus (USB) port 220 (FIG. 3A) to enable the medical device 201 to communicate with a computing system through a wired connection, and/or a jack (not shown) for receiving a plug of a charging cord or adapter (not shown). The access opening 218 thus enables the medical device 201 to be charged and/or connected to a computing system without the need to remove the sleeve 200.

The sleeve 200 is preferably constructed of a durable material (e.g., an elastic polymer) that can stretch and conform to the contours of the medical device 201. However, in some embodiments, the sleeve 200 may be formed of a rigid or semi-rigid material. In yet other embodiments, the sleeve may comprise one or more portions that comprise a rigid or semi-rigid material and one or more other portions that comprise an elastic material. In some embodiments the sleeve 200 may be transparent or translucent, while in other embodiments the sleeve 200 may be opaque. For example, the sleeve 200 may comprise any of a variety of materials, including, but not limited to, polyurethane, polypropylene, polyethylene, polyethylene terephthalate, polyvinyl chloride, polyvinylidene chloride, polystyrene, polyamide, polycarbonate, silicone, neoprene, and copolymers or combinations thereof. The material of the sleeve 200 is preferably resistant to common cleaning and disinfecting solutions, such as, for example, water, an enzyme active powdered detergent that is a concentrated anionic detergent, such as TERGAZYME®, bleach (e.g. up to 50% concentration), isopropyl alcohol (ISA), Pine Quat 64 Disinfectant (e.g. 100% concentration), 64 General Purpose Disinfectant (e.g. 100% concentration), VirkonS (e.g. up to 10% concentration to warm water), Ali-Flex (e.g. 100% concentration), Windex (e.g. 100% concentration), Softsoap (e.g. approximately 2% concentration to water), etc.

With further reference to FIG. 4, the back panel 206 of the sleeve 200 comprises a first closure 222 adjacent the ingress/egress opening 208 and a second closure 224 adjacent the access opening 218. Each of the illustrated closures 222, 224 is substantially rectangular, but in other embodiments they could be any shape. The first closure 222 is configured to selectively cover the ingress/egress opening 208, and the second closure 224 is configured to selectively cover the access opening 218, as described below.

The first closure 222 comprises a separate piece that is secured to the back panel 206 along a first edge 226, while the second closure 224 comprises a separate piece that is secured to the end panel 216 along a first edge 228. However, in alternative embodiments either or both of the closures 222, 224 may be integrally formed with the body 202. Dimensions of each closure 222, 224 are sufficient to enable each closure 222, 224 to completely cover its respective opening 208, 218. Adhesive(s) may be applied to either or both of the first and second closures 222, 224 and/or to either or both of the back panel 206 and the end panel 216. The adhesive(s) enable the closures 222, 224 to be secured to their respective panels 206, 216 while covering their respective openings 208, 218.

In one embodiment, a first adhesive 230 is applied to the first closure 222 and/or to the back panel 206, and a second adhesive 232 is applied to the second closure 224, and/or to the end panel 216, and/or to the back panel 206 adjacent the access opening 218, and the first and second adhesives 230, 232 have different adhesion strengths. For example, the first adhesive 230 may have greater adhesion strength than the second adhesive 232. In such an embodiment, the second closure 224 may be repeatedly adhered to and peeled from the back/end panel(s) 206, 216 so that any ports covered by the second closure 224 can be repeatedly accessed and the access opening 218 subsequently resealed. But the first adhesive 230 is preferably strong enough that the first closure 222, once sealed over the ingress/egress opening 208, cannot be peeled away from the back panel 206 without tearing the first closure 222 and/or the back panel 206. This feature discourages the end user from trying to remove the medical device 201 from the sleeve 200, which could cause the medical device 201 to become soiled or contaminated. In some embodiments, each of the closures 222, 224 comprises an adhesive on the side that is to be adhered to the sleeve 200. A disposable peel-away backing paper (not shown) may cover the adhesive backing on each of the closures 222, 224 to prevent the closures 222, 224 from adhering to any surfaces prior to being secured to the sleeve 200, and to prevent the adhesive backings from attracting and adhering any debris prior to being secured to the sleeve 200.

The protective sleeve 200 described above allows the medical device 201 to be used for multiple patients, with a new protective sleeve 200 applied to the medical device 201 for each patient. The protective sleeve 200 is disposable and is intended for single-patient use. Using a new protective sleeve 200 for each patient helps prevent cross-contamination from patient to patient. The protective sleeve 200 also protects the medical device 201 from contamination and liquid ingress.

FIG. 3B illustrates the protective sleeve 200 and the medical device 201 in combination with acoustic spacers 203. In the illustrated embodiment, the medical device 201 includes a pair of speakers 205 located at opposite corners 207 of one end of the medical device 201. The speakers 205 are configured to emit audible tones, such as tones to alert the patient to various conditions. The protective sleeve 200 overlies the speakers 205. To reduce the attenuation of sound emanating from the speakers 205, the acoustic spacers 203 may be interposed between the medical device 201 and the protective sleeve 200 at the corners 207, as further discussed below.

Each acoustic spacer 203 includes first and second segments 209, 211 that extend in perpendicular directions from a junction 213. Each acoustic spacer 203 is oriented such that the junction 213 aligns with its respective corner 207 of the medical device 201, with the first and second segments 209, 211 extending along perpendicular sides of the medical device 201, as shown in FIG. 3B. The acoustic spacers 203 create spacing between each of the speakers 205 and the protective sleeve 200, thereby reducing the extent to which the protective sleeve 200 muffles sound from the speakers 205.

In other embodiments, the acoustic spacer may have any of a variety of shapes and dimensions that allow it to be interposed between the medical device 201 and the protective sleeve 200. For example, in some embodiments the acoustic spacer may have any of a variety of shapes (e.g., oval, circle, rectangle, square, triangle, pentagon, hexagon, octagon, etc.) and dimensions that conform to a portion of the perimeter (or the entire perimeter) of a speaker.

In certain embodiments, the acoustic spacers 203 may be integral with a housing of the medical device 201. In other embodiments, the acoustic spacers 203 may be separate pieces that are securable to the housing of the medical device 201. For example, each of the acoustic spacers 203 may include an adhesive backing to facilitate adhering the acoustic spacers 203 to the medical device 201. The acoustic spacers 203 may be part of a kit that also comprises the protective sleeve 200, as described in further detail below with respect to the embodiment of FIG. 4C. In yet other embodiments, the acoustic spacers may be integral with the body 202 of the protective sleeve 200 and positioned at a location that allows them to be interposed between the medical device 201 and the protective sleeve 200 at a region near one or more speakers.

Figure 4A:
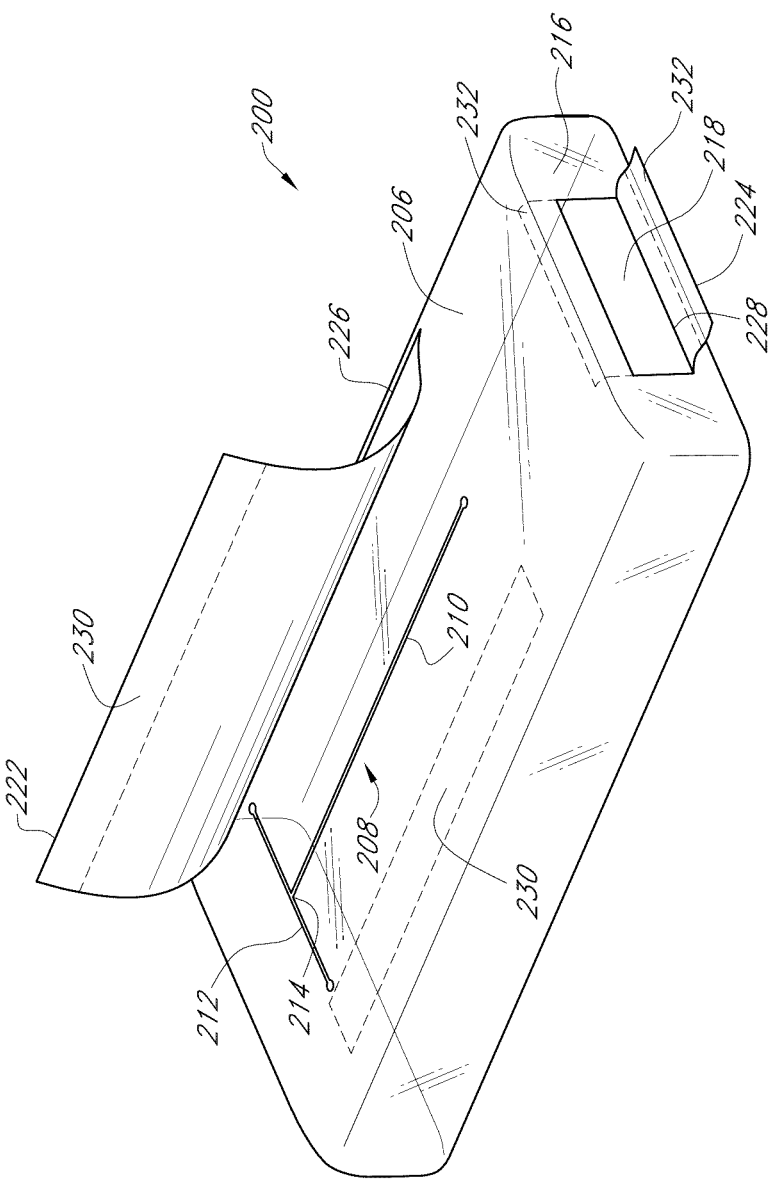
FIG. 4A is a rear perspective view of the protective sleeve of FIG. 2.
Figure 4B:
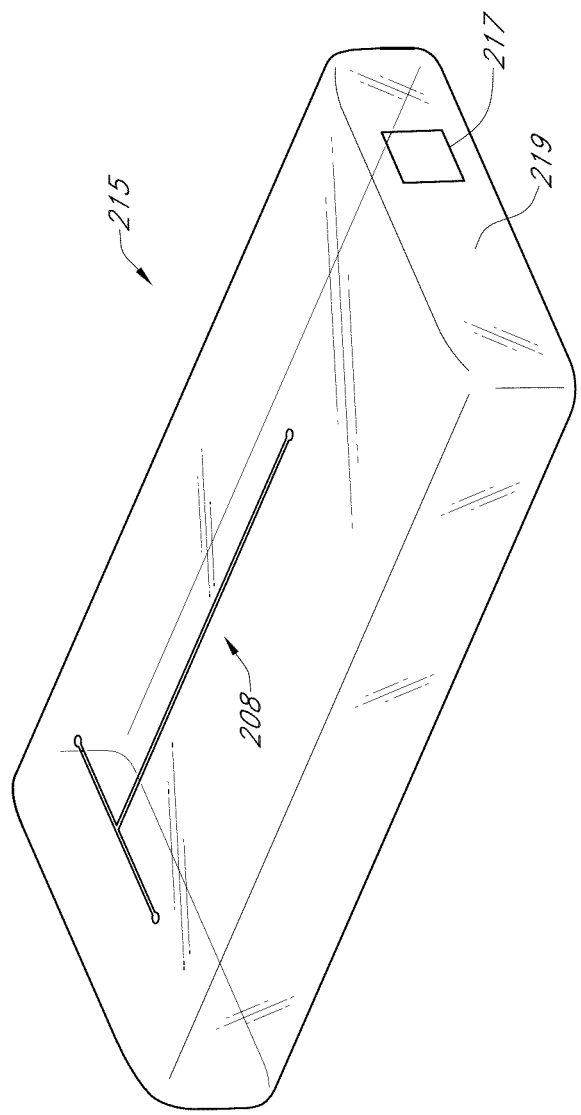
FIG. 4B is a rear perspective view of another embodiment of a protective sleeve for receiving a medical device.

FIG. 4B illustrates another embodiment of a protective sleeve 215 for receiving a medical device. The sleeve of FIG. 4B is similar to the protective sleeve 200 of FIGS. 2-4. Thus, common features will not be described here. The sleeve 215 of FIG. 4B includes an access opening 217 in an end panel 219 of the protective sleeve 215. The access opening 217 is sized and located so as to provide access to a port of the medical device (not shown), such as a USB port.

Figure 4C:
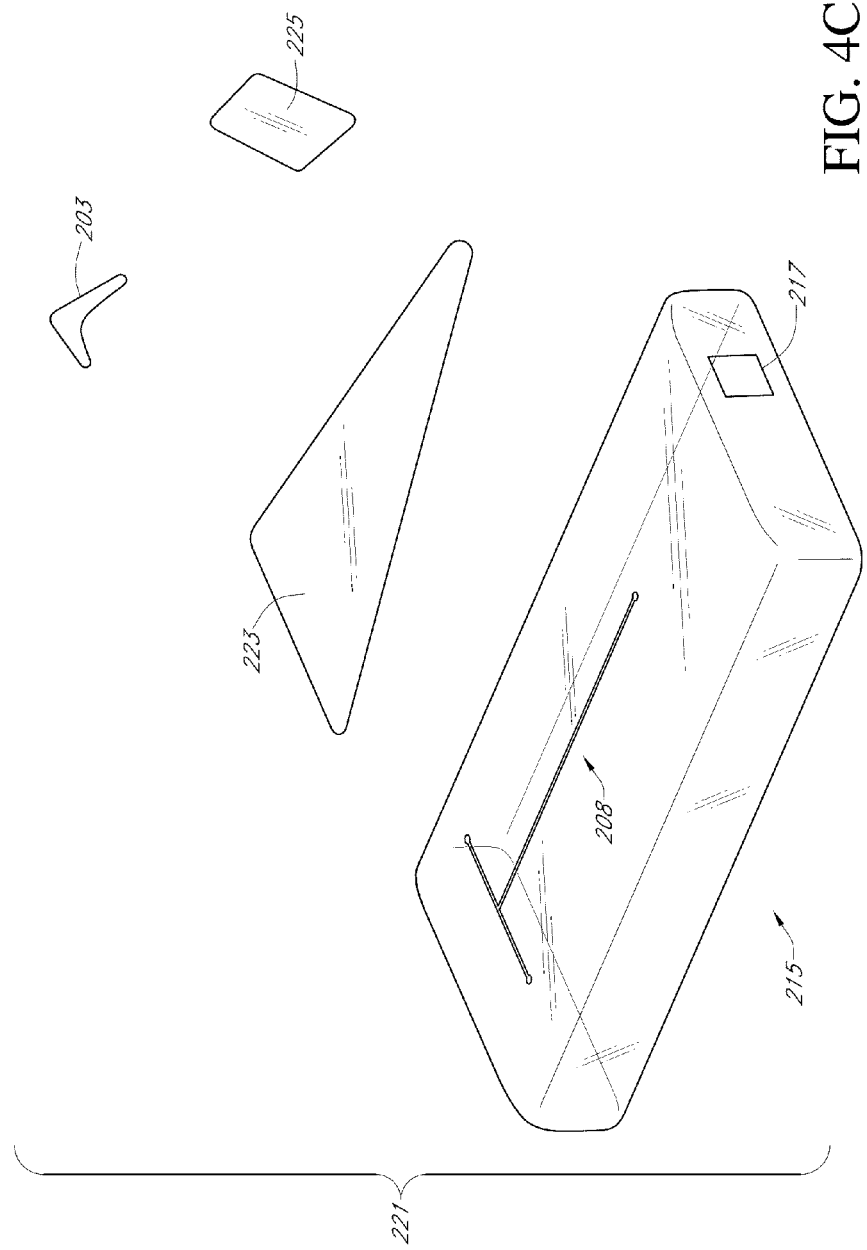
FIG. 4C is perspective view of a kit including the protective sleeve of FIG. 4B, one of the acoustic spacers of FIG. 3B, and closures configured for use with the sleeve of FIG. 4B.
Figure 4D:
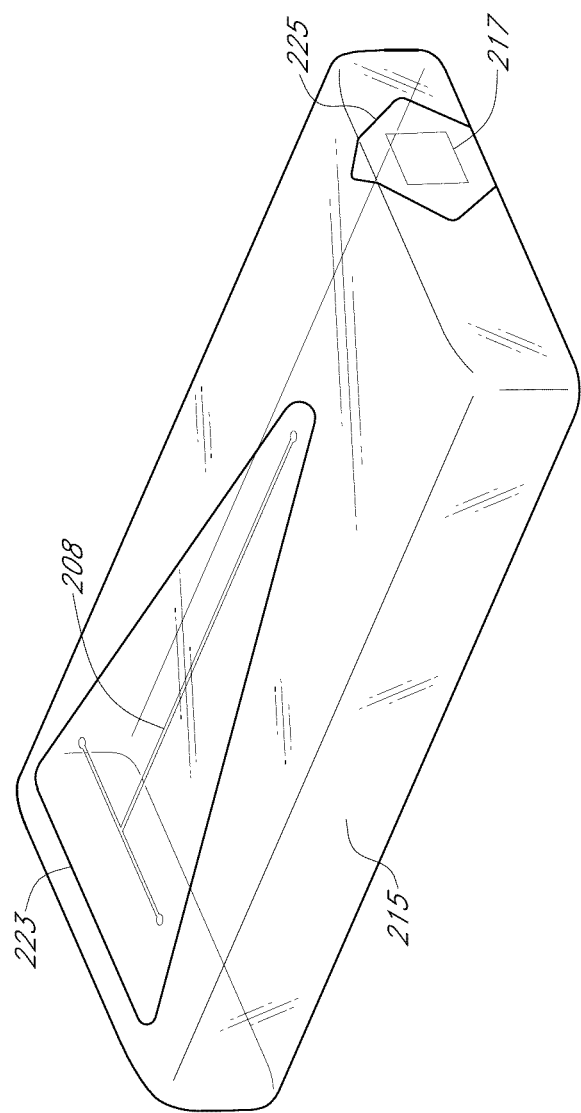
FIG. 4D is a rear perspective view of the sleeve of FIG. 4B and the closures of FIG. 4C.

FIG. 4C illustrates a kit 221 including the protective sleeve 215 of FIG. 4B, one of the acoustic spacers 203 of FIG. 3B, and closures 223, 225 configured to overlie and seal the ingress/egress opening 208 and the access opening 217. A first one of the closures 223 is shaped as a triangle, and is configured to overlie and seal the ingress/egress opening 208, as shown in FIG. 4D. A second one of the closures 225 is shaped as a rectangle (e.g., a square), and is configured to overlie and seal the access opening 217, as also shown in FIG. 4D. Each of the closures 223, 225 may include an adhesive backing so that the closures 223, 225 adhere to the sleeve 215 and seal the openings 208, 217. A disposable peel-away backing paper (not shown) may cover the adhesive backing on each of closures 223, 225 to prevent the closures 223, 225 from adhering to any surfaces prior to being secured to the sleeve 215, and to prevent the adhesive backings from attracting and adhering any debris prior to being secured to the sleeve 215.

The closures 223, 225 may be single-use, such that once a closure 223, 225 is adhered to the sleeve 215 and later removed from the sleeve 215, it is not reused thereafter. In such embodiments, one suitable material for the closures 223, 225 is FasCal® 400 series multi-purpose screenprint film including a removable, acrylic-based adhesive, available from Avery Dennison. In such embodiments, the adhesive may be the same for each of the closures 223, 225. In other embodiments, the closures 223, 225 may comprise an adhesive backing that allows the closures to be peeled off from and re-adhered to the sleeve 215 multiple times.

Protective Cases

Figure 5:
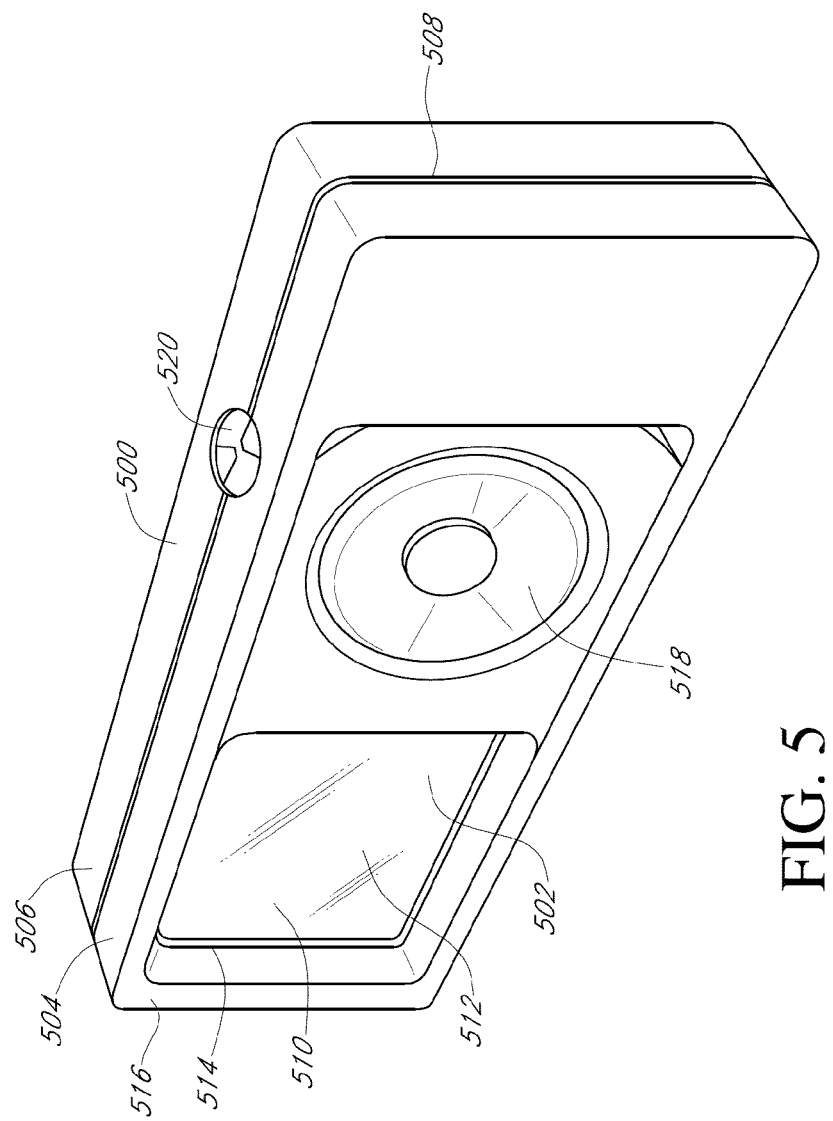
FIG. 5 is a front perspective view of one embodiment of a case for receiving a medical device.
Figure 6:
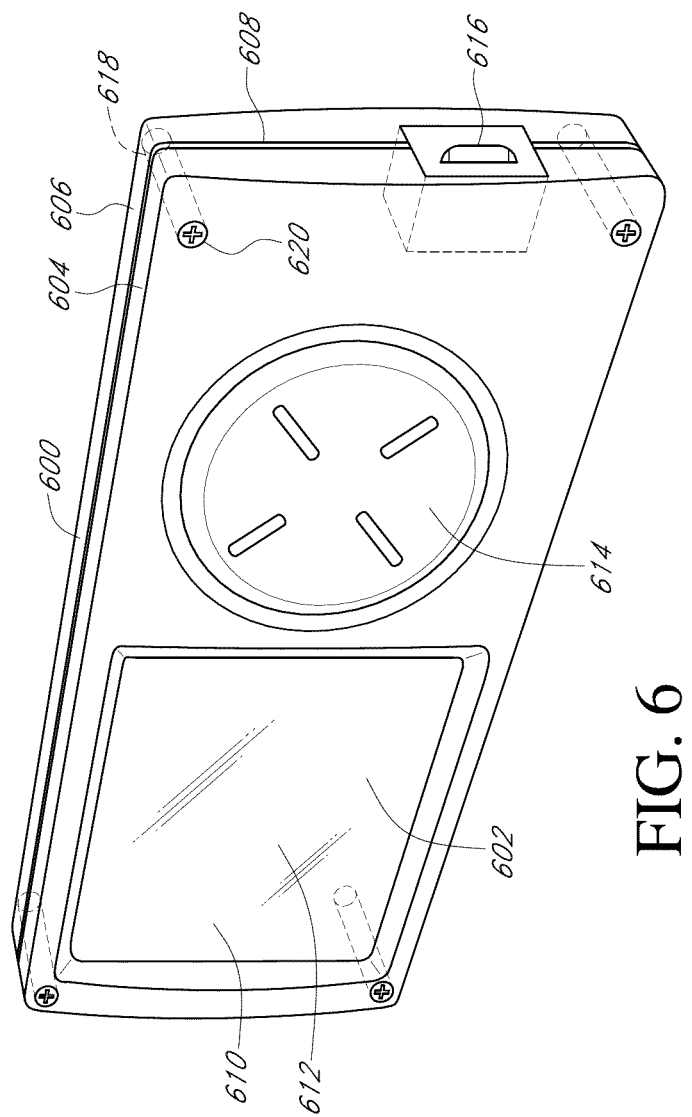
FIG. 6 is a front perspective view of another embodiment of a case for receiving a medical device.

FIGS. 5 and 6 illustrate embodiments of protective cases 500, 600 for receiving a medical device 502, 602 to reduce the risk of contamination of the medical device 502, 602. The case 500, 600 preferably resists penetration of contaminants into an interior of the case 500, 600 so that such contaminants cannot reach the medical device 502, 602 contained within the case 500, 600. Each case 500, 600 further includes a mechanism that at least discourages, if not prevents, the end user from opening the case 500, 600, which would expose the medical device 502, 602 to contaminants.

With reference to FIG. 5, one embodiment comprises a case 500 having a front portion 504 and a back portion 506. The front and back portions 504, 506 are securable to one another with the medical device 502 contained within an interior space defined by the mated front and back portions 504, 506. A gasket 508 may be received about a periphery of the junction of the front and back portions 504, 506 to resist moisture penetration into the interior space of the case 500. The gasket 508 may be of a resilient, moisture resistant material, such as silicone, latex, rubber, and the like.

The front portion 504 of the case 500 of FIG. 5 includes a transparent or translucent window 510 through which a display 512 of the medical device 502 is visible. The window 510 is received within a frame 514 defined by an opening in the front portion 504. Edges of the window 510 are preferably secured to the frame 514 in a moisture-tight fashion to resist moisture penetration into the interior space of the case 500. The window 510 may be constructed from any suitable material that is durable and transparent or translucent, such as, for example, plastic, polycarbonate, and the like. As illustrated in FIG. 5, the window 510 is preferably recessed beneath a front surface 516 of the case 500 in order to make it less likely that the window 510 will get scratched.

The front portion 504 of the case 500 of FIG. 5 further includes a touch pad 518. The location of the touch pad 518 corresponds to the location of a touch pad (not visible in FIG. 5, but located behind the touch pad 518) on the medical device 502. The user can manipulate the touch pad 518 on the case 500 by pressing on any area of it with his or her finger(s) and/or thumb(s), and the digital pressure applied is transmitted to the touch pad on the medical device 502 to thereby enable the user to control the operation of the medical device 502. For example, in some embodiments the touch pad 518 on the case 500 may be constructed of a flexible and resilient material, such as, for example, silicone, latex, rubber, and the like. In other embodiments the touch pad 518 on the case 500 may be constructed of a rigid or semi-rigid material, such as, for example, plastic, polycarbonate, and the like.

Edges of the touch pad 518 on the case 500 are preferably secured to the case 500 in a moisture-tight fashion to resist moisture penetration into the interior space of the case 500. The case 500 of FIG. 5 preferably includes one or more openings or ports (not shown) that enable the user to access any ports on the medical device 502. For example, the medical device 502 may include a Universal Serial Bus (USB) port to enable the medical device 502 to communicate with a computing system through a wired connection, and/or a jack for receiving a plug of a charging cord or adapter.

The front and back portions 504, 506 of the case 500 further include a locking mechanism that deters the user from opening the case 500. For example, in the illustrated embodiment, a lock 520 is located in an upper right-hand corner of the front and back portions 504, 506, and overlaps the junction of front and back portions 504, 506. When in a locked position, the lock 520 prevents the case 500 from being opened. Preferably, the patient is not provided with a key to unlock the lock 520, so that the patient is discouraged from trying to open the case 500, which could cause the medical device 502 inside to become contaminated. Another person, such as a physician who provides the medical device 502 to the patient, preferably possesses the key so that when the patient returns the medical device 502 to the physician at the end of a trial period the physician can open the case 500 and remove the medical device 502 from the case 500 for cleaning and disinfecting.

The structure of the lock 520 may vary in complexity. For example, in some embodiments the lock 520 may comprise something as simple as a removable threaded member (e.g. a bolt, a screw, and the like). In such embodiments, the lock 520 may be "opened" with a tool (e.g. a screwdriver, an Allen key, and the like) that mates with the head of the threaded member. In other embodiments, the lock 520 may be more complex, such as one requiring a key to open (e.g. a warded lock, a pin tumbler lock, a wafer tumbler lock, a disc tumbler lock or Abloy lock, a lever tumbler lock, and the like). In still other embodiments, the lock 520 may comprise a combination lock, a time lock, or any other type of lock.

FIG. 6 illustrates another embodiment of a protective case 600 for receiving a medical device 602 to reduce the risk of contamination of the medical device 602. Like the embodiment of FIG. 5, the case 600 of FIG. 6 includes a front portion 604 and a back portion 606, a gasket 608 around the junction of the front and back portions 604, 606, a window 610 through which the display 612 of the medical device 602 is visible, and a touch pad 614. An end of the case 600 includes a port 616 through which the user may insert a plug of a USB cable. Other ports (not shown) may also be provided for connecting other cables/devices, such as a power cord. Although not shown in the drawings, in some embodiments, the case 600 includes a separate plug that is shaped and sized to fit the port 616 and that may be used to provide the medical device 602 with a liquid tight seal when the port 616 is not in use. By establishing a liquid-tight seal through the use of the plug, the case 600 can be cleaned and/or disinfected many times without exposing the medical device 602 to cleaning or disinfecting solutions. Although not shown in the drawings, in other embodiments the case 600 comprises a flap that is integrally formed with the body of the case. The flap may be configured to have an unlocked and a locked position. When in the unlocked position, the flap may be opened to allow access to the port 616. Conversely, when in the locked positioned, the flap is closed and provides the medical device 600 with a liquid tight seal. In still other embodiments, closures comprising adhesives may be used to seal off the port 616 when it is not in use.

Each corner of the case 600 includes a threaded opening 618 for receiving a fastening member, such as a screw 620. The screws 620 are received in the threaded openings 618 that extend through the front portion 604 and at least partially through the back portion 606 to secure the front and back portions 604, 606 to one another. In some embodiments, the opening through the front portion 604 may not be threaded. Also, other fastening members, such as may be used instead of the screws 620.

The screws 620 provide a deterrent that discourages the patient from opening the case 600. A head of each screw 620 may include a standard feature that can be engaged by one or more common tools, such as a hex key or a screwdriver (flathead or Phillips-head). Alternatively, the head of each screw 620 may be configured such that it will only mate with a special tool that may not be readily available to the patient. In either case, the presence of the screws 620 provides a visual reminder to the patient that it is undesirable for him or her to open the case 600, thereby helping to prevent contamination of the medical device 602.

The illustrated shapes and configurations of the cases 500, 600 of FIGS. 5 and 6 are merely examples that are tailored to receive medical devices 502, 602 having the illustrated shapes, configurations, features, etc. For other medical devices having different shapes, configurations, features, etc., a given case according to the present embodiments would be shaped and configured differently than as illustrated in FIGS. 5 and 6 in order to accommodate such other medical devices. Such changes in shape, configuration, etc. are within the scope of the present embodiments.

As discussed above, the cases 500, 600 described above with reference to FIGS. 5 and 6 restrict access to the medical device. They also cover the medical device and allow the exterior of the case to be cleaned and disinfected without damaging the functionality of the medical device. Once attached to the medical device, the case makes the unit water resistant and resistant to common cleaning and disinfection solutions and brushes. Without the case, the unit may be prone to electronics damage from liquid ingress. Further, without the case, the medical device may be prone to being scratched, dented, cracked, etc.

In some embodiments, the protective cases 500, 600 described above are resistant to common cleaning and disinfecting solutions, such as, for example, water, TERGAZYME®, bleach (e.g. up to 50% concentration), isopropyl alcohol, (ISA), etc. The protective cases are preferably made of a durable, impact-resistant plastic, and fit to the contours of the medical device. Once attached to the medical device, the cases cannot be easily removed without a tool. This feature makes the cases a semi-permanent attachment to the medical device and deters the user from removing the medical device from the cases. The protective cases have one or more access ports that allow the user to easily access any ports on the medical device. Any ports in the cases are preferably closable or coverable to enhance the water resistance of the cases. The protective cases may be used multiple times by multiple patients. The cases are preferably cleaned and disinfected between patients.

The protective cases 500, 600 described above are preferably designed to be effectively cleaned and disinfected. The following features allow the cases to be effectively cleaned and disinfected: As few grooves as possible, any grooves present are large enough to clean with wipes, as few nooks and crannies as possible, an optional antimicrobial coating, water resistance so that it can be submerged in common cleaning and disinfection solutions, resistant to cleaning brushes, able to be cleaned with moistened wipes (i.e. no brush required), and able to withstand 100 wipes with 10% bleach solution and 100 wipes with 70% isopropyl alcohol.

The protective cases 500, 600 described above preferably provide the following characteristics: Ingress Protection Rating of IPX6 or greater, full device functionality inside case (e.g. does not attenuate sound substantially, maintains access to charge port, no impact on RF performance, no impact on IEC 60601 certification of the medical device, etc.), scratch resistance, fog resistance, reduced bulkiness, little to no impact on shipping configuration/validation, and semi-permanent attachment (e.g. can only be removed with a special tool).

The protective cases described above allow the medical device to be used for multiple patients. The protective case is preferably durable so that it may be used multiple times by multiple patients, preferably being cleaned and disinfected between patients. The protective cases also preferably protect the medical device from liquid ingress, and preferably protect the medical device from common cleaning and disinfecting solutions. The protective cases also prevent the medical device from getting scratched or damaged during normal use.

While the description above refers to a receiver of a CGM system (illustrated in FIG. 3A), the present embodiments are not limited to a receiver. The present embodiments are equally adaptable for use with any medical device, such as, for example, a transmitter of a CGM system, any other component of an analyte monitoring system, or any other medical device.

Cleaning and Disinfecting Methods

Certain of the present embodiments comprise methods for cleaning and disinfecting a medical device. Generally, cleaning the device involves removing soil from the device and preparing the device for disinfection. In certain embodiments, cleaning the medical device reduces protein concentration on surfaces of the medical device to less than about 6.4 $\mu g/cm^2$, and reduces hemoglobin concentration on surfaces of the medical device to less than about 2.2 $\mu g/cm^2$. Disinfection involves inactivating microbial organisms and/or viruses on the device, rendering the device safe for use by another patient. In certain embodiments, disinfecting the medical device achieves the following reductions in the concentration of various microbes on surfaces of the electronic device, as compared to a pre-disinfected state: duck hepatitis B virus greater than about 3 $\log_{10}$ reduction, *klebsiella pneumonia* greater than about 6 $\log_{10}$ reduction, *staphylococcus aureus* greater than about 6 $\log_{10}$ reduction, *escherichia coli* greater than about 6 $\log_{10}$ reduction, *pseudomonas aeruginosa* greater than about 6 $\log_{10}$ reduction, and *mycobacterium terrae* greater than about 3 $\log_{10}$ reduction.

Figure 7:
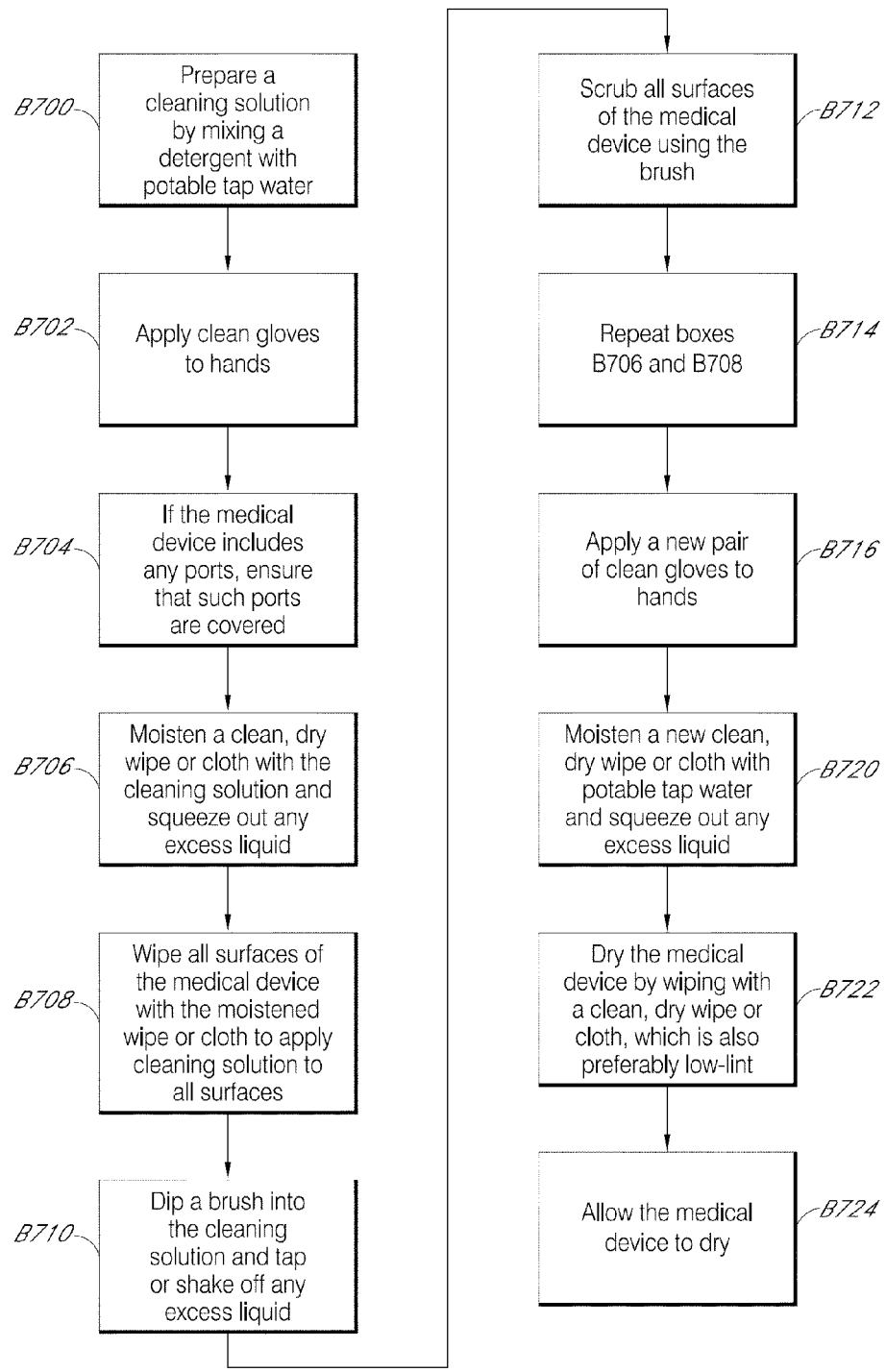
FIGS. 7 and 8 are flowcharts illustrating embodiments of methods for cleaning a medical device.

With reference to FIG. 7, one method for cleaning a medical device comprises the following steps. In box B700, an operator prepares a cleaning solution by mixing a detergent with potable tap water. For example, the detergent may comprise an enzymatic detergent containing one or more of sodium bicarbonate, sodium tripolyphosphate, sodium carbonate, sodium alkybenzene sulfonate, and other non-hazardous ingredients of less than 1% concentration. For example, the detergent may comprise TERGAZYME®, and the cleaning solution may comprise a 1% TERGAZYME® solution. The 1% TERGAZYME® solution may be produced by, for example, mixing 1¼ TBSP TERGAZYME® with ½ gallon of potable tap water.

In box B702, the operator applies clean gloves to his or her hands. The gloves are preferably resistant to chemicals that may be used in the cleaning method. In box B704, if the medical device includes any ports, such as a charging port, a USB (Universal Serial Bus) port, etc., the operator ensures that such ports are covered. For example, the medical device may include a cover for each port, such as a sliding or swinging door. If the medical device does not include a cover or covers, the operator may cover each port with a temporary, single-use, disposable port cover, which is used to protect the medical device during cleaning and disinfection (e.g. a custom or off-the-shelf plug, tape, and the like).

In box B706, the operator moistens a clean, dry wipe or cloth with the cleaning solution and squeezes out any excess liquid. Preferably, the wipe or cloth is also low lint. For example, the wipe or cloth may comprise a microfiber wipe or cloth. In box B708, the operator wipes all surfaces of the medical device with the moistened wipe or cloth to apply cleaning solution to all surfaces. In one embodiment, a method of wiping the medical device may comprise the following steps, in no particular order: folding the wipe into quarters; with a first surface of the wipe, wiping the top of the medical device; refolding the wipe to expose a clean second surface; with the clean second surface wiping all sides of the medical device, refolding the wipe again to expose a clean third surface; and, with the clean third side of the wipe, wiping the bottom of the medical device.

In box B710, the operator dips a brush into the cleaning solution and taps or shakes off any excess liquid. In certain embodiments, the bristles of the brush may be a soft material (e.g. nylon and the like) that will not scratch or haze the surfaces of the medical device. In box B712, the operator scrubs all surfaces of the medical device using the brush. In one embodiment, the operator may scrub the medical device for a minimum duration, such as 15 seconds, 30 seconds, 45 seconds, 60 seconds, etc. Preferably, the operator thoroughly scrubs areas where soil may collect, such as seams and crevices, e.g. around any buttons and/or ports.

In box B714, the operator repeats boxes B706 and B708. In box B716, the operator applies a new pair of clean gloves to his or her hands. In box B720, the operator moistens a new clean, dry wipe or cloth with potable tap water and squeezes out any excess liquid. The operator then wipes all surfaces of the medical device with the moistened wipe. In one embodiment, a method of wiping the medical device may comprise the same steps outlined above with respect to box B708. In box B722, the operator dries the medical device by wiping with a clean, dry wipe or cloth, which is also preferably low-lint. The operator may refold the wipe to expose a dry surface as needed. In box B724, the operator allows the medical device to dry. In certain embodiments, the medical device may be inverted (keypad and screen facing down) for drying, and any ports thereon may remain open. In one embodiment, the operator may allow the medical device to dry for a minimum duration, such as 30 minutes, 45 minutes, 60 minutes, etc.

Figure 8:
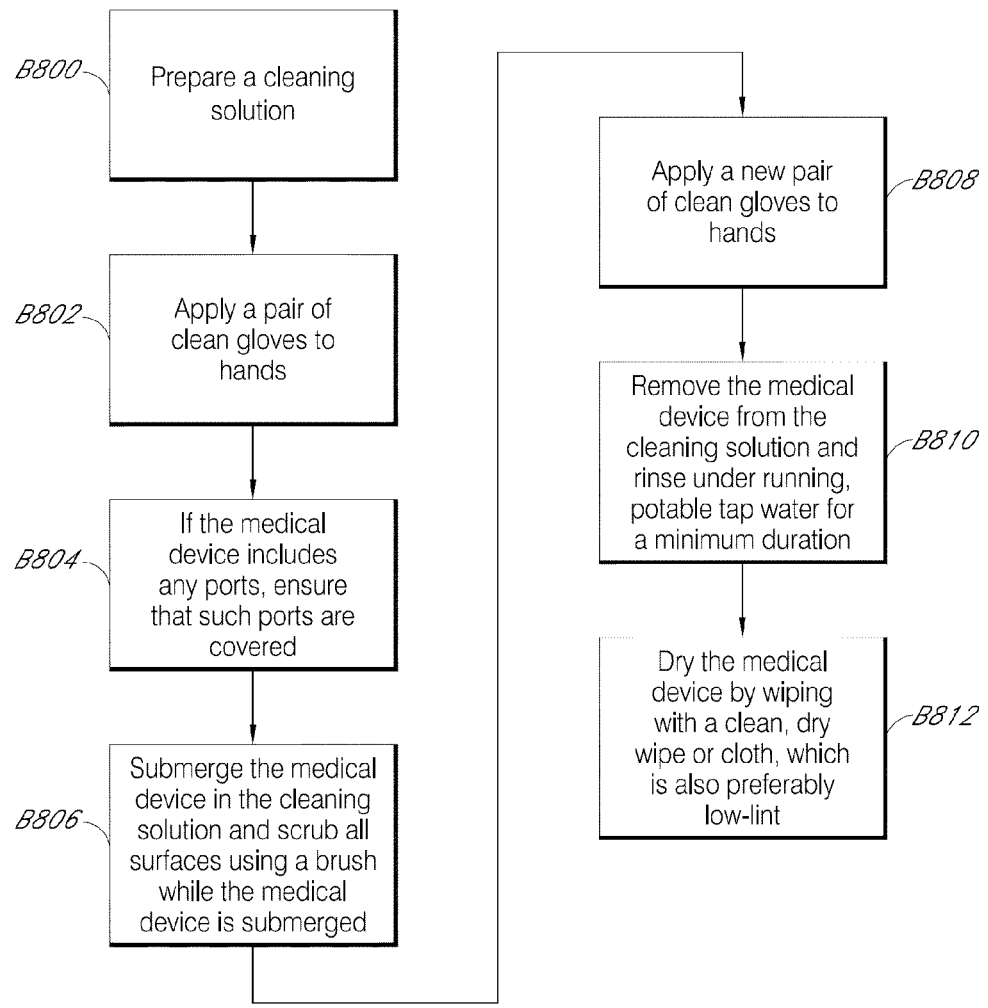

With reference to FIG. 8, another method for cleaning a medical device comprises the following steps. In box B800, the operator prepares a cleaning solution. In certain embodiments, the cleaning solution may be prepared according to the ratios/methods described above with respect to box B700. In box B802, the operator applies a pair of clean gloves to his or her hands. In box B804, if the medical device includes any ports, such as a charging port, a USB (Universal Serial Bus) port, etc., the operator ensures that such ports are covered, similar to box B704 described above. In box B806, the operator submerges the medical device in the cleaning solution and scrubs all surfaces using a brush while the medical device is submerged. The brush and duration of scrubbing may be similar to those described above with respect to boxes B710 and B712. After brushing, the operator leaves the medical device submerged to soak in the cleaning solution for a minimum duration, such as 30 seconds, 45 seconds, 60 seconds, 90 seconds, 2 minutes, etc. In one embodiment, the total duration for which the medical device remains submerged, including scrubbing and soaking, is 3 minutes. In box B808, the operator applies a new pair of clean gloves to his or her hands. In box B810, the operator removes the medical device from the cleaning solution and rinses under running, potable tap water for a minimum duration, such as 5 seconds, 10 seconds, 15 seconds, 20 seconds, 25 seconds, 30 seconds, etc. In box B812, the operator dries the medical device by wiping with a clean, dry wipe or cloth, which is also preferably low-lint. The operator may refold the wipe to expose a dry surface as needed.

Generally, disinfecting the device involves inactivating bacteria, fungi, and/or viruses that may be resident on the medical device. In certain embodiments, the disinfecting methods include a disinfecting solution, which may be, for example, an off-the-shelf spray preparation, which may contain bleach. One such disinfecting solution may be Dispatch® Hospital Cleaner Disinfectant with Bleach, which advantageously has a short contact time and provides for ease of use. In certain embodiments, the disinfecting solution may be contained in an easy-to-use spray bottle.

Figure 9:
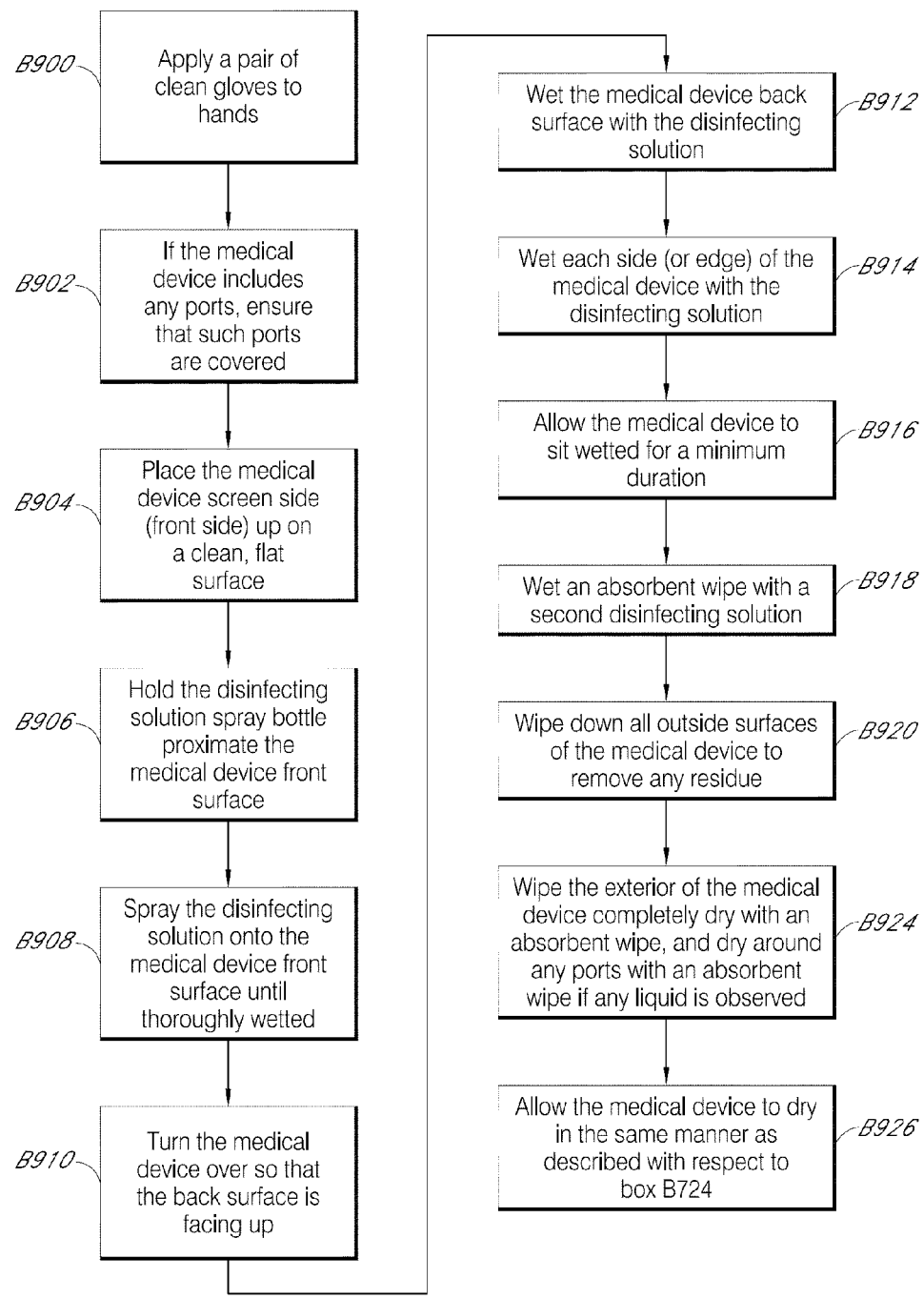
FIGS. 9 and 10 are flowcharts illustrating embodiments of methods for disinfecting a medical device.

With reference to FIG. 9, one method for disinfecting a medical device comprises the following steps. In box B900, the operator applies a pair of clean gloves to his or her hands. In box B902, if the medical device includes any ports, such as a charging port, a USB (Universal Serial Bus) port, etc., the operator ensures that such ports are covered, similar to box B704 described above. In box B904, the operator places the medical device screen side (front side) up on a clean, flat surface. In box B906, the operator holds the disinfecting solution spray bottle proximate the medical device front surface. For example, in one embodiment the operator may hold the spray bottle 6"-8" from the medical device front surface. In box B908, the operator sprays the disinfecting solution onto the medical device front surface until thoroughly wetted. The operator may tilt the medical device if necessary to ensure the disinfecting solution has covered the entire front surface. In box B910, the operator turns the medical device over so that the back surface is facing up. In box B912, the operator wets the medical device back surface with the disinfecting solution in the same manner as in boxes B906 and B908.

In box B914, the operator wets each side (or edge) of the medical device with the disinfecting solution in the same manner as in boxes B906 and B908. However, in certain embodiments, the operator does not wet (or at least does not directly spray) any side of the medical device that includes at least one port. In box B916, the operator allows the medical device to sit wetted for a minimum duration, such as 30 seconds, 45 seconds, 60 seconds, 90 seconds, 2 minutes, 5 minutes, etc.

In box B918, the operator wets an absorbent wipe with a second disinfecting solution, such as a 70% isopropyl alcohol (IPA) solution. In box B920, the operator wipes down all outside surfaces of the medical device to remove any residue, such as bleach residue. In box B922, the operator uncovers any ports that were covered in box B902 and wipes or dabs any liquid residue from interior surfaces of the port(s). Preferably, the operator avoids contacting any metal components of the port(s) with the second disinfecting solution so as to avoid causing an electrical short.

In box B924, the operator wipes the exterior of the medical device completely dry with an absorbent wipe, and dries around any ports with an absorbent wipe if any liquid is observed. In box B926, the operator allows the medical device to dry in the same manner as described with respect to box B724.

Figure 10:
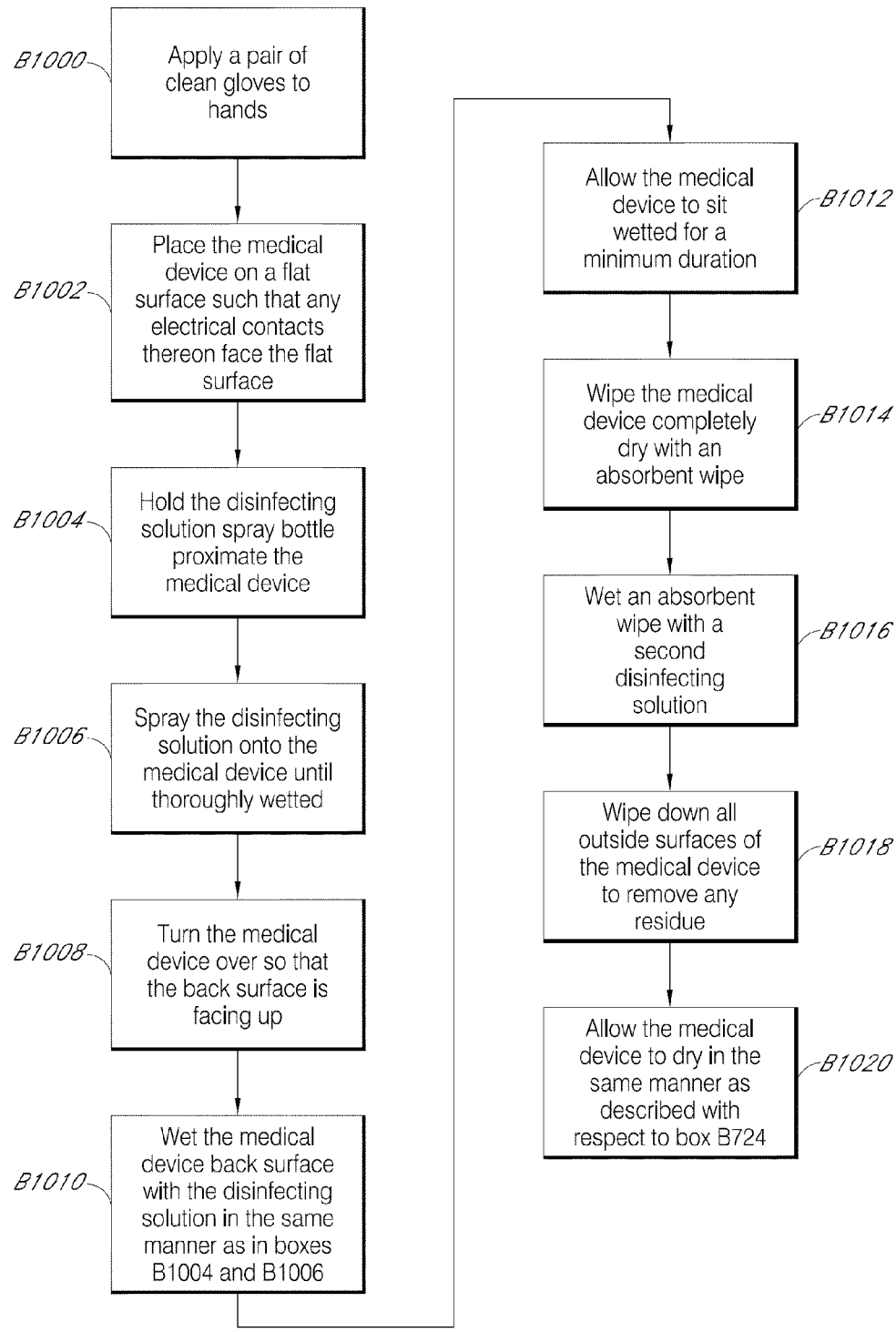

With reference to FIG. 10, another method for disinfecting a medical device comprises the following steps. In box B1000, the operator applies a pair of clean gloves to his or her hands. In box B1002, the operator places the medical device on a flat surface such that any electrical contacts thereon face the flat surface. In boxes B1004 and B1006, the operator wets the medical device front surface with the disinfecting solution in a similar manner as described above with respect to boxes B906 and B908. In box B1008, the operator turns the medical device over so that the electrical contacts face up. In box B1010, the operator wets the medical device back surface with the disinfecting solution in the same manner as in boxes B1004 and B1006.

In box B1012, the operator allows the medical device to sit wetted for a minimum duration, such as 30 seconds, 45 seconds, 60 seconds, 90 seconds, 2 minutes, 5 minutes, etc. In box B1014, the operator wipes the medical device completely dry with an absorbent wipe. In box B1016, the operator wets an absorbent wipe with a second disinfecting solution, such as a 70% isopropyl alcohol (IPA) solution. In box B1018, the operator wipes down all outside surfaces of the medical device to remove any residue, such as bleach residue. In box B1020, the operator allows the medical device to dry in the same manner as described with respect to box B724.

Figure 11:
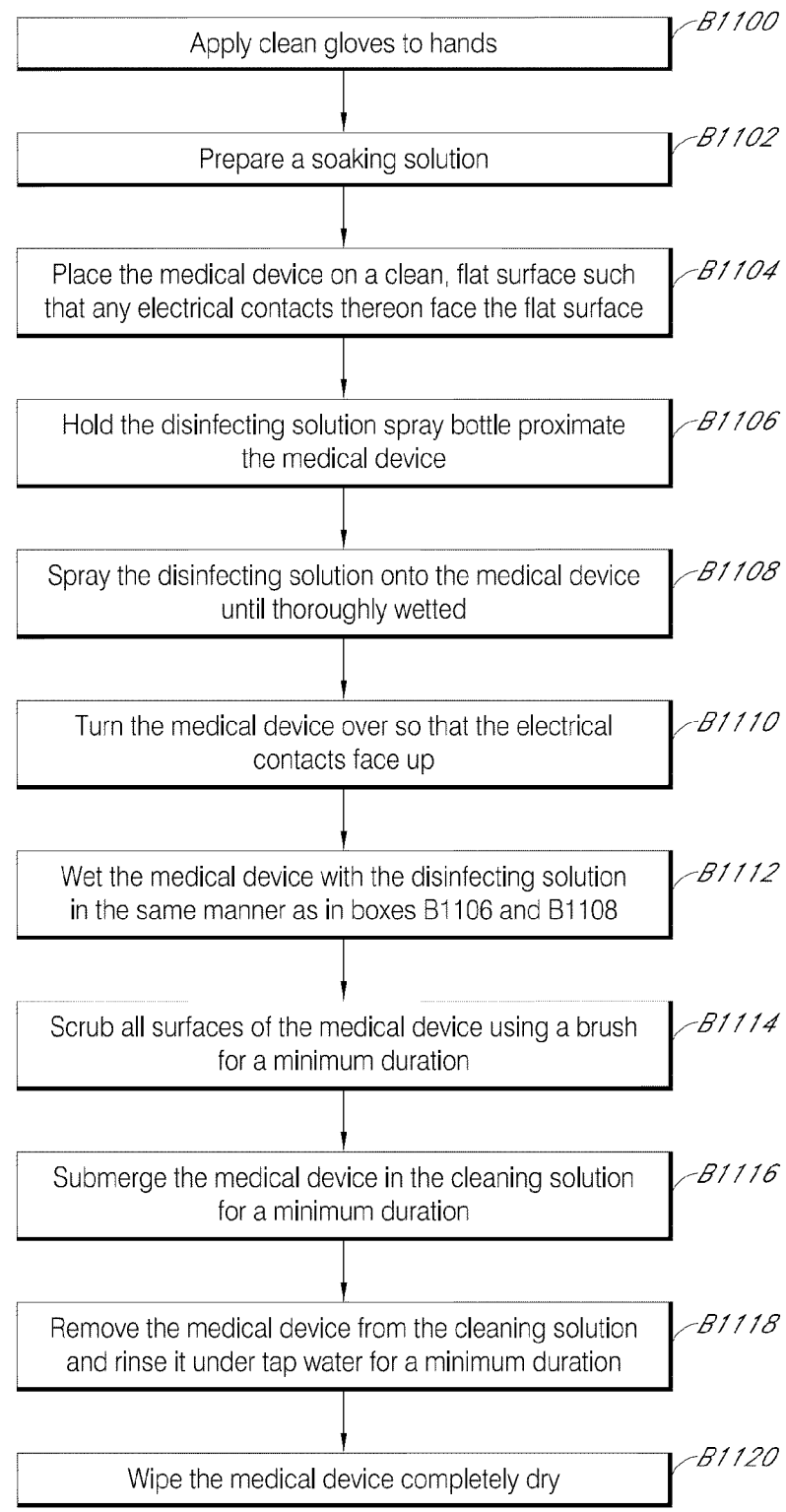
FIG. 11 is a flowchart illustrating another embodiment of a method for cleaning a medical device.

With reference to FIG. 11, another method for cleaning a medical device comprises the following steps. In box B1100, the operator applies a pair of clean gloves to his or her hands. In box B1102, the operator prepares a soaking solution by adding enough bleach solution to a container to submerge the medical device. In box B1104, the operator places the medical device on a flat surface such that any electrical contacts thereon face the flat surface. In boxes B1106 and B1108, the operator wets the medical device front surface with the disinfecting solution in a similar manner as described above with respect to boxes B906 and B908. In box B1110, the operator turns the medical device over so that the electrical contacts face up. In box B1112, the operator wets the medical device back surface with the disinfecting solution in the same manner as in boxes B1104 and B1106.

In box B1114, the operator scrubs all surfaces of the medical device using a brush for a minimum duration. In box B1116, the operator submerges the medical device in the cleaning solution for a minimum duration. In box B1118, the operator removes the medical device from the cleaning solution and rinses it under tap water for a minimum duration. In box B1120, the operator wipes the medical device completely dry.

Figure 12:
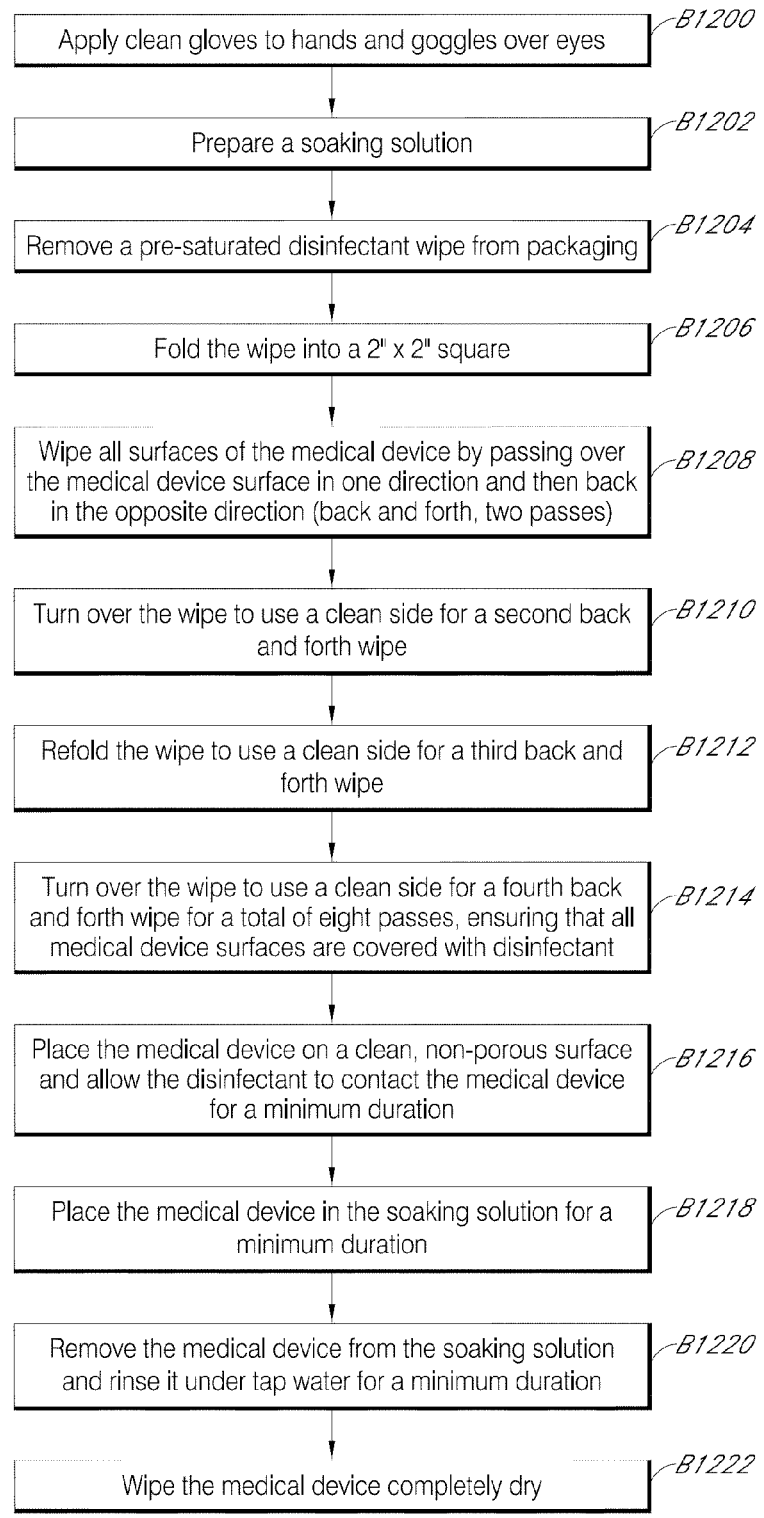
FIG. 12 is a flowchart illustrating another embodiment of a method for disinfecting a medical device.

With reference to FIG. 12, another method for disinfecting a medical device comprises the following steps. In box B1200, the operator applies a pair of clean gloves to his or her hands and goggles over his or her eyes. In box B1202, the operator prepares a soaking solution by adding enough bleach solution to a container to submerge the medical device. In box B1204, the operator removes a pre-saturated disinfectant (e.g. bleach) wipe from its packaging. In box B1206, the operator folds the wipe into a 2"×2" square. In box B1208, the operator wipes all surfaces of the medical device by passing over the medical device surface in one direction and then back in the opposite direction (back and forth, two passes). In box B1210, the operator turns over the wipe to use a clean side for a second back and forth wipe. In box B1212, the operator refolds the wipe to use a clean side for a third back and forth wipe. In box B1214, the operator turns over the wipe to use a clean side for a fourth back and forth wipe for a total of eight passes, ensuring that all medical device surfaces are covered with disinfectant (e.g. bleach).

In box B1216, the operator places the medical device on a clean, non-porous surface and allows the disinfectant to contact the medical device for a minimum duration. In box B1218, the operator places the medical device in the soaking solution for a minimum duration. In box B1220, the operator removes the medical device from the soaking solution and rinses it under flowing tap water for a minimum duration. In box B1222, the operator wipes the medical device with a cloth until it is completely dry.

In a further embodiment, an electronic medical device, such as the electronic medical device 201 shown in FIG. 3A, may include a coating of a liquid repellant (e.g., hydrophobic) substance. The coating may surround all exposed electrical surfaces of the electronic medical device and seal any cracks, fissures, etc. The coating may be invisible to the human eye. For example, one suitable coating is available from Liquipel of Santa Ana, Calif. In one study, tests were conducted comparing the effectiveness of the above-described coating in allowing a medical device to be cleaned and in a variety of cleaning solutions without sustaining damage. In this study, five DexCom G4® Platinum receivers comprising the test group were coated with Liquipel. Another five DexCom G4® Platinum receivers comprising the control group were not coated with Liquipel. The study comprised 10 cleaning cycles, in which each cleaning cycle comprised the following steps: (1) wiping the receiver with a detergent; (2) brushing the receiver while exposed to the detergent; (3) wiping the receiver with the detergent; (4) wiping the receiver with water; (5) wiping dry the receiver; (6) setting the receiver for five minutes; (7) spraying the receiver with bleach; (8) setting the receiver for five minutes; (9) wiping dry the receiver; (10) wiping the receiver with alcohol; (11) wiping dry the receiver; (12) setting the receiver for one hour. With the test group, all five receivers underwent the 10 cleaning cycles without suffering any failures. With the control, however, only one of the four receivers did not suffer failure after the 10 cleaning cycles. Of the five receivers in the control group, two suffered USB failure by the fourth cleaning cycle, one suffered USB failure by the eighth cleaning cycle, and one suffered an unintended reset (i.e., stuck in manufacturing mode) by the second cleaning cycle. The study clearly demonstrated the viability of coating a medical device with a liquid repellant substance (e.g., Liquipel) to transform it into a device that can be exposed to common agents, such bleach, and/or water, without sustaining damage.

As expected, positive control receivers exhibited failures due to liquid ingress.

a. 80% failure rate after 10 cycles of cleaning and disinfection.

As expected, negative control receivers continued to function properly due to no liquid exposure.

a. 0% failure rate.

Liquipel was effective at protecting the receiver from damage due to liquid ingress.

a. All Liquipel receivers continued to function properly after 10 cycles of cleaning and disinfection.

b. 0% failure rate after 10 cycles of cleaning and disinfection

In an example process of applying the coating to the electronic medical device, the placed in an airtight chamber from which substantially all air is evacuated to create a vacuum. Once the vacuum has been established, the coating material may be injected into the chamber in liquid form. Upon entering the vacuum chamber, the liquid becomes a gas. Plasma is then introduced into the vacuum chamber. The plasma decomposes the liquid repellant molecules, polymerizing them to themselves. Air is then reintroduced into the chamber until it returns to atmospheric pressure. The electronic medical device is then removed from the chamber and the process is complete.

The above description presents the best mode contemplated for carrying out the present invention, and of the manner and process of practicing it, in such full, clear, concise, and exact terms as to enable any person skilled in the art to which they pertain to practice this invention. This invention is, however, susceptible to modifications and alternate constructions from those discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

What is claimed is:

1. An enclosure for a receiver of an analyte monitoring system, the enclosure comprising:
    a sleeve configured to receive a receiver having a communication port, wherein the receiver is configured to wirelessly receive sensor data and display glucose concentration information, wherein the sleeve has substantially no impact on RF performance, wherein the sleeve is configured to protect against liquid ingress, wherein the sleeve is sized and shaped to substantially conform to a shape of the receiver;
    a first opening in the sleeve sized and configured to allow for insertion of the receiver into the sleeve and removal of the receiver from the sleeve;
    a second opening in the sleeve, the second opening being located so as to permit access to the communication port when the receiver is received within the sleeve;
    a first cover configured to adhere to a first portion of the sleeve and to cover the first opening; and
    a second cover configured to adhere to a second portion of the sleeve and to cover the second opening.

2. The enclosure of claim 1, further comprising a first adhesive located and configured to secure the first cover to the sleeve at the first portion.

3. The enclosure of claim 2, further comprising a second adhesive located and configured to secure the second cover to the sleeve at the second portion.

4. The enclosure of claim 3, wherein the first adhesive comprises a first peel strength, the second adhesive comprises a second peel strength, and the first peel strength is different than the second peel strength.

5. The enclosure of claim 4, wherein the first peel strength is greater than the second peel strength.

6. The enclosure of claim 4, wherein the first peel strength is great enough to prevent separation of the first cover from the sleeve without tearing the sleeve.

7. The enclosure of claim 1, wherein communication port also serves as a charging port.

8. The enclosure of claim 7, wherein the communication port is a USB port.

9. The enclosure of claim 1, wherein the sleeve comprises a material selected from the group consisting of polyurethane, polyethylene, and low density polyethylene.

10. The enclosure of claim 1, wherein the sleeve comprises a first portion comprising a first material and a second portion comprising a second material.

11. The enclosure of claim 10, wherein the second material has greater stiffness than the first material.

12. The enclosure of claim 10, wherein the first portion comprises a material selected from the group consisting of polyurethane, polyethylene, and low density polyethylene.

13. The enclosure of claim 10, wherein the second portion comprises a material selected from the group consisting of polycarbonate and acrylonitrile butadiene styrene.

14. The enclosure of claim 10, wherein the second portion is configured to provide access to the communication port.

15. The enclosure of claim 10, wherein the first opening is surrounded by the first portion, and wherein the second opening is surrounded by the second portion.

16. The enclosure of claim 1, wherein the first opening comprises a first slit that extends in a longitudinal direction, and a second slit that extends in a transverse direction.

17. The enclosure of claim 16, wherein a first end of the first slit corresponds to a lengthwise center of the second slit.

18. A method for reprocessing a reusable receiver of an analyte monitoring system, the method comprising:
    receiving a receiver from a first user, wherein the receiver is contained in a first protective enclosure, wherein the receiver has a communication port, wherein the receiver is configured to wirelessly receive sensor data and display glucose concentration information, wherein the first protective enclosure has substantially no impact on RF performance, wherein the first protective enclosure is configured to protect against liquid ingress, wherein the first protective enclosure is sized and shaped to conform to a shape of the receiver;
    removing the receiver from the first protective enclosure;
    inserting the receiver into a second protective enclosure through an opening in the second protective enclosure, wherein the second protective enclosure has substantially no impact on RF performance, wherein the second protective enclosure is configured to protect against liquid ingress, wherein the second protective enclosure is sized and shaped to substantially conform to a shape of the receiver;

adhering a cover to the second protective enclosure over the opening; and providing the receiver contained within the second protective enclosure to a second user.

19. The method of claim 18, further comprising creating a disinfected field, wherein removing the receiver from the first protective enclosure and placing the receiver in a second protective enclosure are performed in the disinfected field.

20. The method of claim 18, wherein removing the receiver from the first protective enclosure requires tearing the first protective enclosure.

21. The method of claim 18, further comprising cleaning and disinfecting the receiver.

22. The method of claim 18, wherein the receiver is configured to display continuous glucose concentration data over a time period.

23. The method of claim 18, wherein the cover is configured to prevent separation from the second protective enclosure without damaging the second protective enclosure.

24. The method of claim 18, wherein removing the receiver from the first protective enclosure, inserting the receiver into a second protective enclosure through an opening in the second protective enclosure, and adhering a cover to the second protective enclosure over the opening are performed by an individual wearing a glove.

25. The method of claim 24, further comprising disposing the glove.

* * * * *